United States Patent
Morozov

(10) Patent No.: US 7,871,824 B2
(45) Date of Patent: Jan. 18, 2011

(54) FLOW CHAMBER

(75) Inventor: Victor Morozov, Manassas, VA (US)

(73) Assignee: George Mason Intellectual Properties, Inc., Fairfax, VA (US)

(*) Notice: Subject to any disclaimer, the term of this patent is extended or adjusted under 35 U.S.C. 154(b) by 665 days.

(21) Appl. No.: 11/397,911

(22) Filed: Apr. 5, 2006

(65) Prior Publication Data

US 2006/0263269 A1    Nov. 23, 2006

Related U.S. Application Data

(60) Provisional application No. 60/668,078, filed on Apr. 5, 2005.

(51) Int. Cl.
*G01N 35/08* (2006.01)
(52) U.S. Cl. .................... 436/52; 422/33; 422/100; 422/102; 422/296
(58) Field of Classification Search .......... 422/100, 422/102, 33, 296; 436/52
See application file for complete search history.

(56) References Cited

U.S. PATENT DOCUMENTS

2003/0190608 A1* 10/2003 Blackburn ............... 435/6
2004/0048362 A1* 3/2004 Trulson et al. .......... 435/287.2
2004/0189988 A1* 9/2004 Scaduto ................... 356/244

* cited by examiner

*Primary Examiner*—Lyle A Alexander
*Assistant Examiner*—Dennis M White
(74) *Attorney, Agent, or Firm*—David Grossman; Edgar Rodriguez; David Yee

(57) ABSTRACT

A flow chamber having a vacuum chamber and a specimen chamber. The specimen chamber may have an opening through which a fluid may be introduced and an opening through which the fluid may exit. The vacuum chamber may have an opening through which contents of the vacuum chamber may be evacuated. A portion of the flow chamber may be flexible, and a vacuum may be used to hold the components of the flow chamber together.

20 Claims, 22 Drawing Sheets

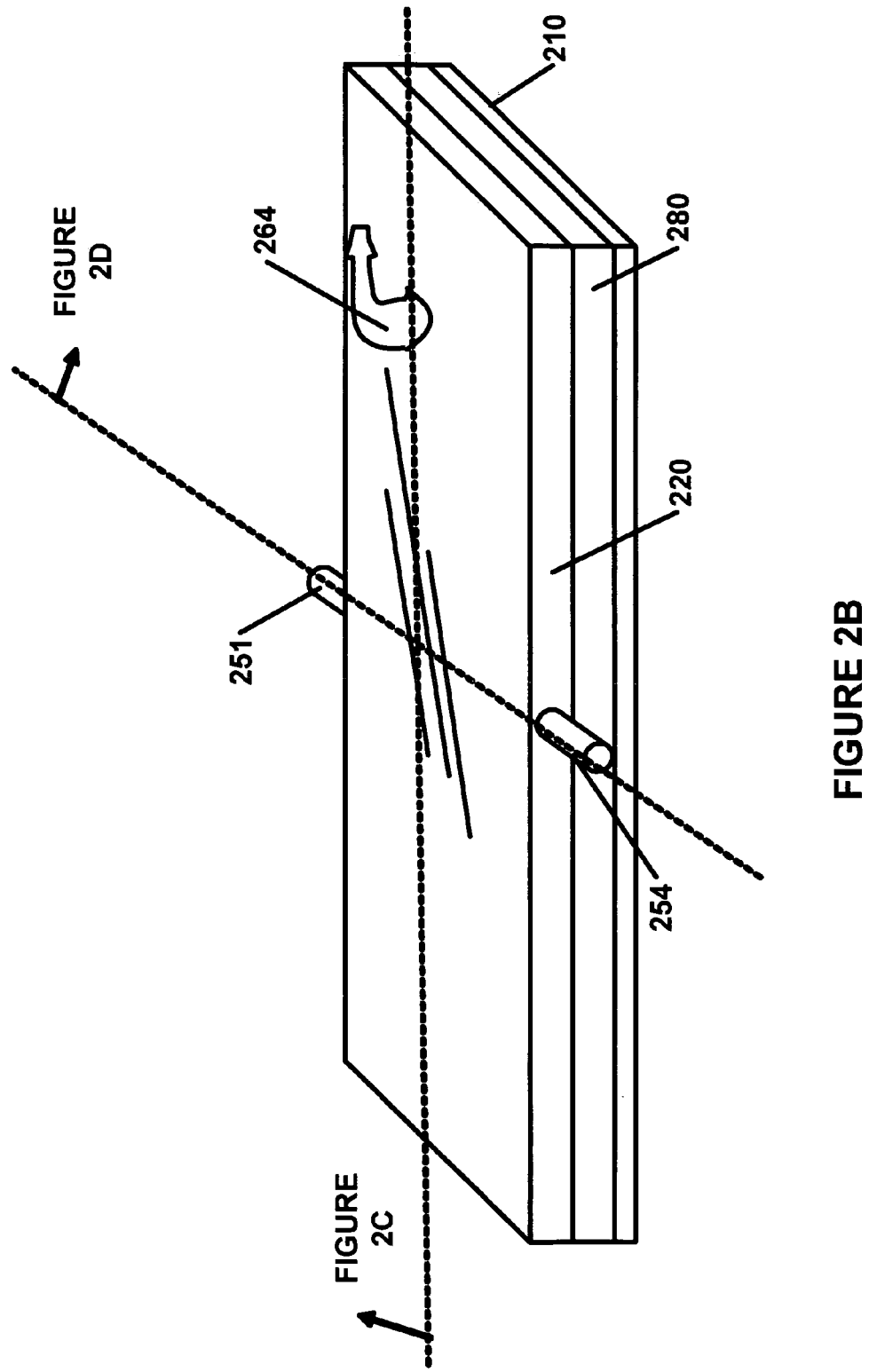

FLOW CHAMBER

CROSS-REFERENCES TO RELATED APPLICATION

This application claims priority of U.S. Provisional Patent Application Ser. No. 60/668,078, filed Apr. 5, 2005.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. DE-F C52-04NA25455 by the United States Department of Energy.

BRIEF DESCRIPTION OF THE DRAWINGS

The following drawings describe some embodiments of the present invention.

FIG. 2B is a perspective view of the second embodiment of the present invention.

DETAILED DESCRIPTION OF EMBODIMENTS

Several embodiments will now be described in detail with reference to the accompanying drawings. It should be understood that the embodiments and the accompanying drawings have been described for illustrative purposes and the present invention is limited only by the claims.

Flow chambers can alternatively be called flow cells. Flow chambers may have an area through which sample flows while they are observed. The area may be called a specimen chamber or, alternatively, a specimen channel. Microfluidic chips can also serve as the area through which a sample flows. Flow chambers can be used for many purposes in sciences and industry. Flow chambers can be used: (1) to facilitate the optical measurements of a series of fluid samples; (2) to study cell culture growth under a controlled condition in a flow chamber called a perfusion chamber; (4) to characterize the adhesion of microspheres, proteins, virus, or enzymes to a surface or other particles; and (4) to scan the surface of a substrate base with functionalized particles moved along the surface under the combined action of shear flow and normal force. Some flow chambers can be mounted on a microscope as a specimen mount. Some flow chambers can be a component of a bigger mechanical system and be used to automate data collection of a series of samples. Some flow chambers can be mounted on a microscope to follow up events inside the specimen chamber. These are just examples of some potential uses of flow chambers. There are many other potential uses of flow chambers.

Figure 1:
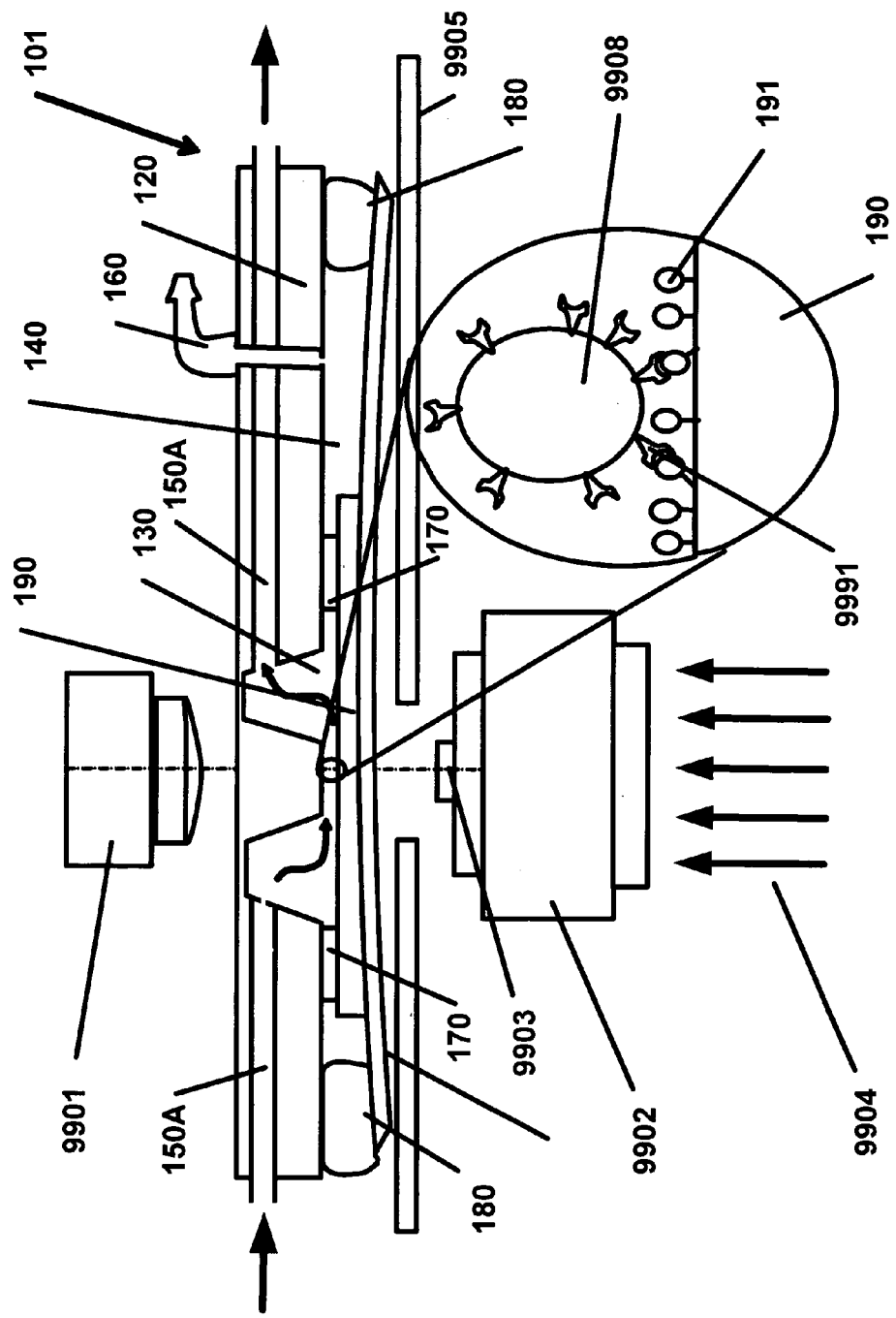
FIG. 1 is a partial sectional view of a first embodiment of the present invention that is mounted on a microscope to scan a microarray surface with functionalized magnetic beads.

FIG. 1 is a partial sectional view of a first embodiment of the present invention that is mounted on a microscope. Not all embodiments of the present invention are adapted to be mounted on a microscope. However, this embodiment is mountable on a microscope.

The assay that is being performed with the first embodiment of the present invention in FIG. 1 is the measurement of the adhesion of antibodies 9991 on functionalized magnetic beads 9908 on antigens 191 on the surface of a microarray 190 under a combined action of a shear stress and magnetic force. In this example, the antibodies 9991 specifically bind to the antigens 191 upon a physical contact between the magnetic beads 9908 and the surface of the microarray 190. Controlled shear stress and magnetic field may be used to make and to break the specific bonding, and to measure the strength of the bond.

A substrate base can be a solid surface like glass or a porous material like a gel or plastic sheet on which, or in which, antigens, antibodies, proteins, DNA, or other particles or functionalities may be positioned. A substrate base is alternatively referred to as a substrate. The word "substrate" may also refer to antigens, antibodies, enzymes or other functionalities which may be printed or positioned on a substrate base. A substrate base that has binding functionalities embedded or positioned in or on them may be called binding substrates. Depending on the experiment or use, inert substrates may be used as well. The surface of a substrate base may be created by coating the surface with a monolayer of particles, or by embedding certain particles into a matrix of porous material. Placing a substrate base in the specimen chamber is one way of positioning a reagent, antigen, or other particles inside a flow chamber. There are other types of substrate bases.

Microarrays are a type of substrate bases. Microarrays can contain a pattern of specific functionalities deposited on a sheet of solid or porous material. Many types of microarrays are made in labs, and some are commercially available. Some microarrays comprises of antigen or antibody micro-spots printed on a surface. Some microarrays have spots of DNA or oligonucleotides. These microarrays may alternatively be referred to as gene chip, DNA microarray, DNA chip, or biochips. Some microarrays may have spots of proteins or other functionalities. Microarray 190 is an example of a substrate base that can be used with the first embodiment of the present invention. One type of microarray 190 may be made by covalent binding anti-rabbit IgG antigen molecules 191 on the surface of a dialysis membrane.

Due to the difference in flow rate of liquid resulting from the contact with the walls of a first chamber or a specimen chamber 130, a shear stress may be applied on any particle suspended in the liquid or particles embedded on a wall of the specimen chamber 130. In the assay shown in FIG. 1, a magnetic bead 9908 is suspended in a fluid that is passing through the specimen chamber 130. Because the magnetic bead 9908 is coated with antibodies 9991, the antibodies 9991 bind to the antigens 191 on the microarray 190 upon its contact with the antigens 191, and the magnetic bead 9908 is arrested on the spot. The shear stress on the magnetic bead 9908 may be controlled by changing the flow rate of the fluid through the specimen chamber 130. If the shear stress on the magnetic bead 9908 overcomes the affinity of the antibody 9991 for the antigens 191, the bond may break and the magnetic bead 9908 washed into the stream of fluid.

Similar approaches can be useful in measuring the adhesion of plant, animal and microbial cells, or that of nano-particles and micro-particles to different surfaces or particles. Such studies can be useful in immunology, clinical studies, and environmental studies. The affinity with which a protein binds to a reactor site of another protein may provide valuable information about the efficiency of protective antibodies, vaccines, and drugs. Microbial adhesion to surfaces may also be used to measure biolfilm formation on structures such as tooth surfaces, ship hulls, and pipelines.

The flow chamber 101, as illustrated, is mounted on a microscope. A conventional optical microscope generally comprises an ocular lens, an objective lens, a stage, and a light source or a reflector. There are several known modes of optical microscopy, including bright-field and dark-field illumination, phase contrast, and fluorescence microscopy. Bright-field illumination microscopy usually produces a dark image of the specimen against a white background. The illumination is usually obtained from a bright surface, a light source, or a reflected light source. Dark-field illumination microscopy usually produces a bright image of the specimen against a dark background. Many known modes of microscopy require a transparent specimen mount. For example, a dark-field microscopy on a conventional optical microscope requires a transparent specimen mount with enough open space on both sides of the specimen mount to place the objective lens close to the specimen on one side and to place the dark-field illuminator on the other side. For example, the first embodiment of the present invention as shown in FIG. 1 has open spaces to both sides of the flow chamber 101.

Dark-field microscopy may be used in the assay shown in FIG. 1. Some parts of the microscope are shown in FIG. 1. The flow chamber 101 is mounted on a stage 9905 of the microscope. An objective lens 9901 is placed above the flow chamber 101. A light source provides light that goes through a dark-field illuminator 9902. The light is reflected inside the dark-field illuminator 9902, so that only light scattered on the magnetic beads 9908 can reach the objective lens 9901. A magnet 9903, which may be placed on the dark-field illuminator 9902, draws the magnetic beads 9908 close to the antigens 191 without interfering with the illumination.

To mount a flow chamber on a microscope, the flow chamber may need to have a compact design to fit on the stage of the microscope. If the flow chamber is not transparent, it may not be compatible with some modes of optical microscopy. The distance between an objective lens and a specimen chamber may affect the power of magnification that is possible with the flow chamber. Compact design of the flow chamber also may save precious samples. For a shear stress experiment, the shear stress may be a function of the thickness of the specimen chamber. The first embodiment of the present invention discloses a flow chamber that is adapted for use on a microscope. However, not all embodiments of the present invention are adapted for use on a microscope.

The flow chamber 101 shown in FIG. 1 has three openings 150a, 150b, 160. The third opening 160 communicates with a second chamber or a vacuum chamber 140. For this embodiment, two O-ring spacers 170, 180 are arranged in concentric arrangement, and O-ring spacer 170 separates the specimen chamber 130 from the vacuum chamber 140. The first member 110 and the second member 120 may be transparent so that light rays 9904 reflected by a dark-field illuminator 9902 pass through the first member 110, the substrate base 190, and the liquid sample inside the specimen chamber 130. Some light may be scattered on the magnetic beads 9908. The scattered light may pass through the second member 120 to reach the objective lens 9901. Because of the transparency and the compact design of the flow chamber 101, this embodiment of flow chamber may be suitable for use with most standard modes of optical microscopy, including bright-field and dark-field illumination, phase contrast, and fluorescence microscopy. In addition, this embodiment may allow use of the flow chamber 101 on a microscope with a magnet 9903 that can be used to manipulate the magnetic beads 9908.

In operation, a vacuum chamber 140 may be evacuated through the third opening 160, for example, by using a commercially available vacuum pumps which may be coupled to the third opening with a plastic tube. A vacuum can also be created with a syringe. There are many other ways to create a vacuum. Evacuating the content of vacuum chamber 140 lowers the internal pressure inside the vacuum chamber 140. A portion of the first member 110 may be deformed by the vacuum, and the first member 110 and the second member 120 may be held together by the atmospheric pressure. The vacuum chamber 140 may contain air, but other gases or fluids may produce the same effect.

Fluid may enter the specimen chamber 130 through the opening 150a and flow out of the chamber 130 through the opening 150b. The fluid may be introduced into the specimen chamber 130 with a syringe, peristaltic pump, or other mechanisms to produce a steady stream and to control the flow rate and the shear stress. When a suspension of magnetic beads 9908 coated with antibodies 9991 is introduced into the specimen chamber 130, the magnet 9903 may make the magnetic beads 9908 move toward the surface of the microarray 190, dragging the beads 9908 on the surface of the microarray 190 until the antibodies 9991 bind with the antigens 191 and the beads 9908 tether on the spot. The user may increase the flow rate of the fluid in the specimen chamber 130, imposing additional shear stress on the magnetic bead 9908. If the shear stress overcomes the affinity of the antibodies 9991 for the antigens 191, the magnetic bead 9908 may be washed into the fluid. The movement of the magnetic beads 9908 may be observed with the microscope, or be recorded and digitally analyzed with the use of a computer.

The dimension of the first embodiment of the present invention as illustrated in FIG. 1 may be as follows. The first opening 150a which communicates with the specimen chamber 130 has a diameter of 0.4-1.0 mm, and the specimen chamber 130 is approximately 0.03-0.05 mm in height, 1.5 mm in width, and 2 mm in length. The second member 120 is approximately 1.3 mm in thickness, 25 mm in width, and 30 mm in length. The microarray 190 is approximately 0.03 mm in thickness and 6 mm in diameter. The first member 110 is approximately 1.0 mm in thickness, 25 mm in width, and 75 mm in length. These dimensions are given as examples only, and the present invention is not intended to be limited to these dimensions.

Flow chambers do not have to be used on a microscope. Some flow chambers may be a part of an automated device that gathers data for a series of samples. An automated device may be designed to contain several flow chambers so that data may be collected simultaneously on several chambers.

Some flow chambers may be used for flow cytometry. The essential principle of flow cytometry is to suspend particles in a fluid phase to study the particle. Currently, a typical experiment could involve passing a light source through the sample to gather information for each particle by measuring the spectral bands of light, which represent the detection of various chemical or biological components.

Another use of a flow chamber may be to create a shear stress environment where a cell can be grown. For example, human, animal, or microbial cells can be suspended in fluid moving through a flow chamber to simulate the type of environments common in a blood circulation system. Similarly, cells may be attached to a suitable substrate and then be placed into a specimen chamber to measure the critical shear stress level necessary to detach the cells from the substrate.

Another possible use of a flow chamber is to analyze multiple samples. In contrast to using a regular microscopic slide, with a flow chamber, a series of samples may be introduced to the specimen chamber. With an automated data collecting system, the use of a flow chamber may speed up the assay. The flow chamber, for example, may be a part of an apparatus equipped with microscopic lenses, a camera that records data, and a computer that processes the digital image recorded by the camera. This enumeration may be modified. There are various other uses for a flow chamber.

Figure 2A:
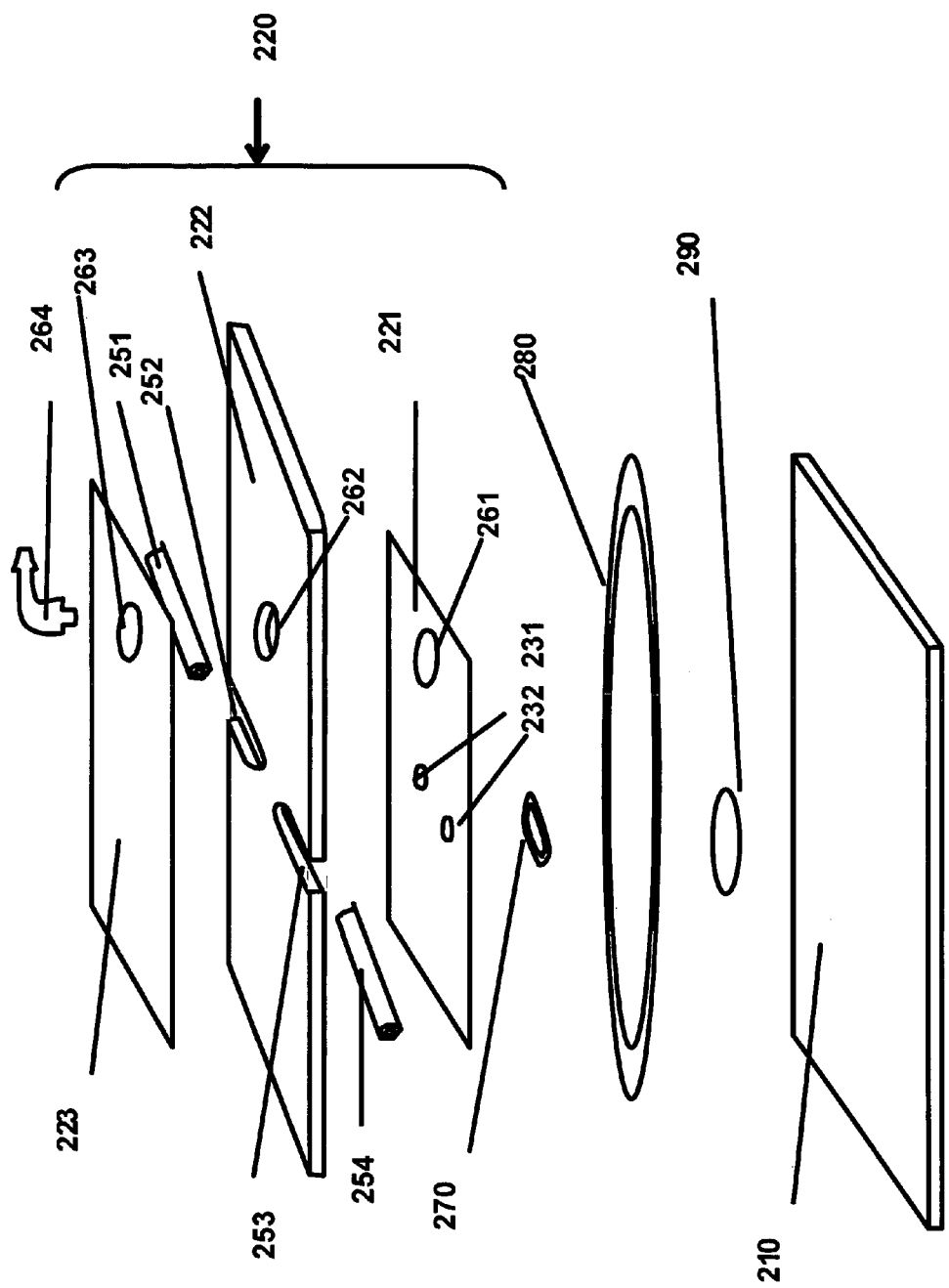
FIG. 2A is an exploded perspective view of a second embodiment of the present invention.

FIG. 2A presents an exploded perspective view of a second embodiment of a flow chamber according to the present invention. The second member 220 comprises three sub-plates 221, 222 and 223. These sub-plates 221, 222 and 223 may be made out of many different materials. For example, they may be made out of thin glass sheets or plastic sheets. The sub-plates 221, 222 and 223 may be glued together to form the second member 220. The holes 261, 262 and 263 may form an opening that communicates with a vacuum chamber. The nozzle 264 may allow the opening to be sealed when a vacuum is created in the vacuum chamber by evacuating the content of the chamber. The sub-plate 222 may have two cut-out sections 252 and 253 which form parts of channels that may communicate with the specimen chamber. A sample may be added through a straw, tube, or hypodermic needle 254 attached to opening 254. The solution may flow through 231, into the specimen chamber defined by sub-plate 221, an inner O-ring 270 and the first member 210. The sample can then exit through an opening 232, a channel formed by a cut-out section 252, a straw, a tube, or a hypodermic needle 251.

The inner O-ring 270 and the outer O-ring 280 may be made in a variety of shapes and out of a variety of materials. One example is a rectangular elastic polymer ring that can maintain an air-tight vacuum chamber when a vacuum is created. The substrate base 290 may be made out of a variety of material. For example, microarrays with an antibody could be used for an immunoassay. The substrate base 290 does not have to be a sheet. It may be a matrix of solid porous material. For certain experiments, a substrate base 290 does not have to be used.

One way to make the second member 220 of the second embodiment of the present invention as shown in FIG. 2A is as follows. The first sub-plate 221 and the second sub-plate 223 may be made from glass coverslips of approximately 0.130 mm in thickness, 25 mm in width, and 30 mm in length. These coverslips are commercially available for specimen mount on a microscope. Holes 263, 261, 231 and 232 of approximately 0.3-1.0 mm in diameter may be etched on the first and second sub-plates 221 and 223 by covering a cover slip with wax, making scratches or marks on the wax, and exposing the waxed coverslip to a solution of concentrated hydrofluoric acid. The second sub-plate 222 may be made from a standard commercial microscopic glass slide that is approximately 1 mm in thickness, 25 mm in width, and 75 mm in length. A hole 262 and a cut-out section 252 may be made using a method such as etching on the glass slide or by machining with a diamond drill.

Stainless steel tubes may be used as connectors 251 and 254 for an inlet and outlet openings that communicate with the specimen chamber. A hose barb polypropylene tube fitting may be used as a nozzle 264 for the vacuum chamber. These hose barbs are also commercially available, for example, from Small Parts, Inc. of Miami Lakes, Fla.

Sub-plates 221, 222, 223, inlet 251 outlet 254, and nozzle 264 may be glued together, for example, using a photo-activated glue. The second member 220 has a resulting thickness of approximately 1.3 mm.

O-rings 270 and 280 may be made from a polymer film such as sealing tape made from polyolefin from 3M adhesive technology. The inner O-ring 270 may be approximately 0.03-0.05 mm in height, 1.5 mm in width, and 2 mm in length. The outer O-ring 280 may be rectangular in shape and approximately 0.05-0.1 mm in height, 25 mm in width, and 30 mm in length.

For certain experiments or uses like the immunoassay shown in FIG. 1, a substrate base 290 of approximately 6 mm in diameter and 0.03 mm in thickness may be placed inside the specimen chamber. The thickness of the inner O-ring 270 may be adjusted to account for the thickness of the microarray. For certain experiments and uses, a substrate base may not be necessary.

In operation, a microarray 290 may be placed on the first member 210. The second member 220 may be placed on the top of the first member 210. The air may be evacuated via the nozzle 264 from the vacuum chamber defined by the two O-rings 270 and 280, the first member 210 and the second member 220. The atmospheric pressure should hold first member 210 and second member 220 together. The inner O-ring 270 should provide a hermetic connection and keep first member 210 and second member 220 at a certain distance. The flexible portion of the first member 210 may deform, applying a pressure on the inner O-ring 270 and thus keeping the specimen chamber air-tight. The thickness of the formed specimen chamber may be determined by the thickness of the inner O-ring 270. There are many ways to vary the shape and size of the specimen chamber. The dimensions and the method of preparing the second embodiment are provided as examples only, and are not intended to limit the embodiments.

Figure 2C:
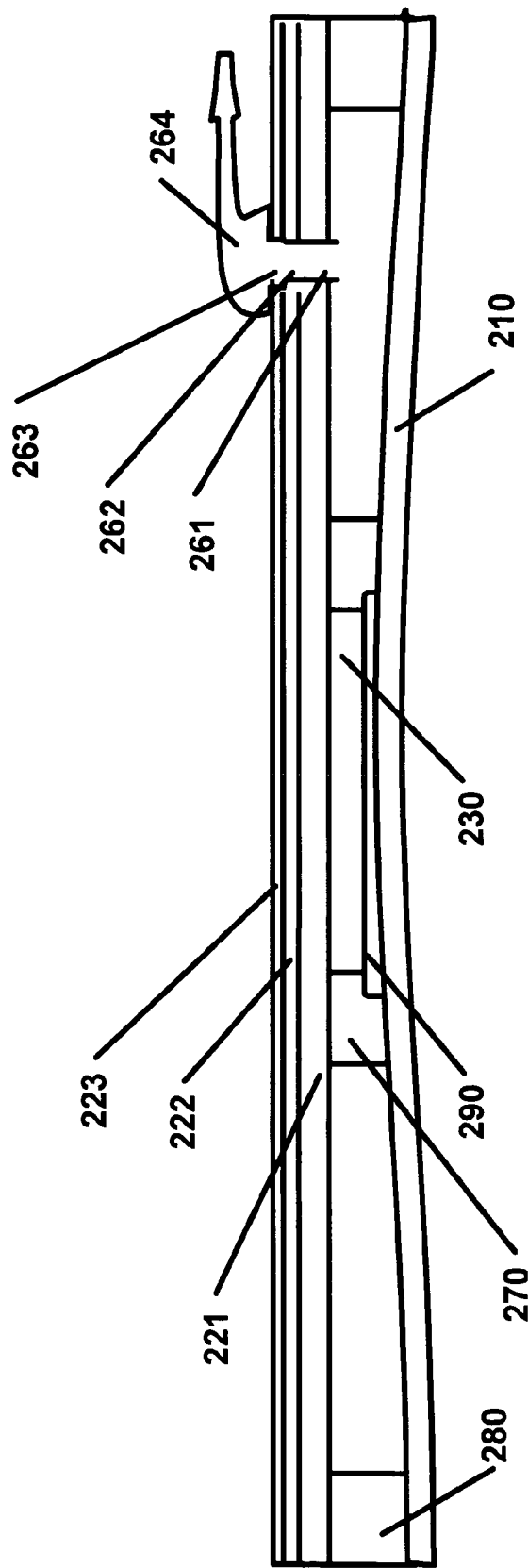
FIG. 2C is a sectional view of the second embodiment of the present invention.

FIG. 2B is a perspective view of the second embodiment shown in FIG. 2A when the flow chamber is assembled. For this particular embodiment, first member 210 and second member 220 are rectangular in shape. However, embodiments with different shapes and sizes are a part of the present invention. FIG. 2B and FIG. 2C are cross-sectional views of the second embodiment shown in FIG. 2A. Dotted lines in FIG. 2B indicate where the cross-sections in FIGS. 2B and 2C were taken from.

FIG. 2C is a sectional view of the second embodiment shown in FIG. 2B. In this illustration, the content of the vacuum chamber 240 is already evacuated through an opening defined by holes 261, 262 and 263 sub-plates 221, 222 and 223. A specimen chamber 230 is defined by an inner O-ring 270, the first member 210, and the second member 220. As shown, a substrate base 290 is inserted in the specimen chamber 230. The inner O-ring 270 presses down on the substrate base 290, so that the substrate base 290 will not move during an assay. The deformation of first member 210 forms a narrow specimen chamber 230.

Figure 2D:
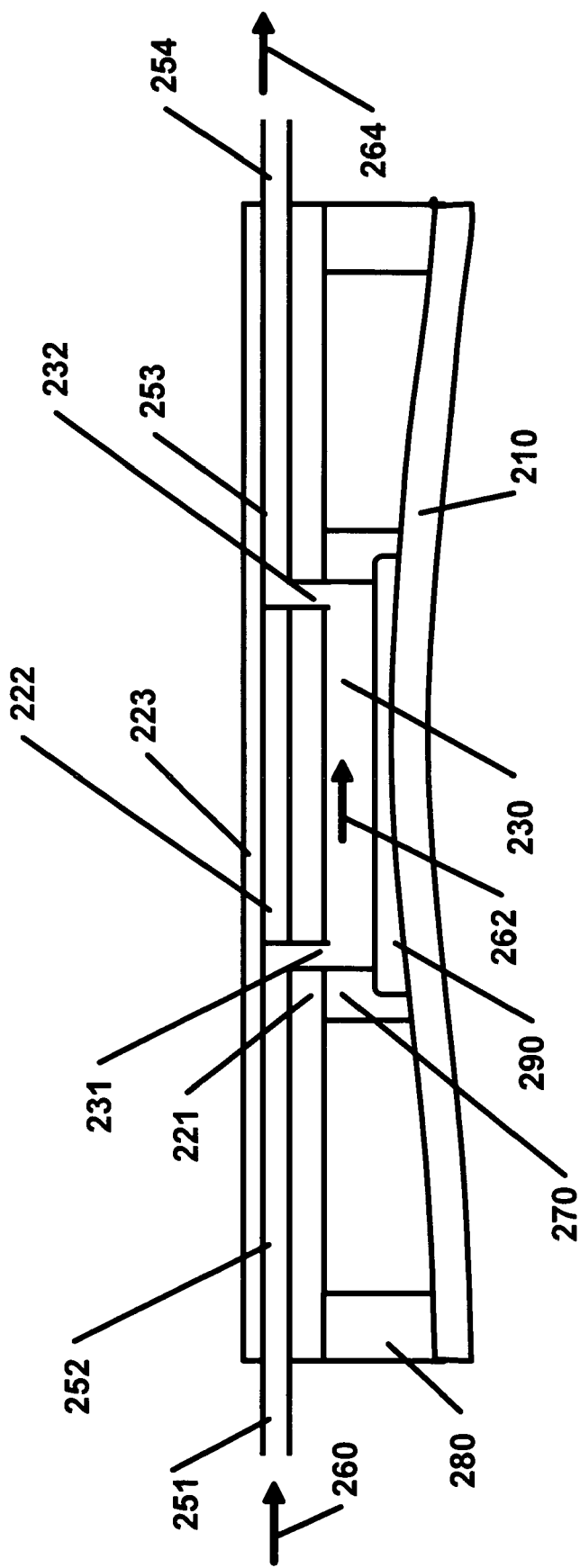
FIG. 2D is a sectional view of the second embodiment of the present invention.

FIG. 2D is a second sectional view of the second embodiment shown in FIG. 2b. This sectional view shows an inlet channel and an outlet channel formed by cut-out sections 252 and 253. The inlet and the outlet channels communicate with the specimen chamber 230. The direction of fluid passing through the specimen chamber 230 is shown with arrows 260, 262 and 264.

Some flow chambers may be made from two parallel plates. These flow chambers may be called parallel-plated flow chambers. A section of the parallel plates are used as a specimen chamber through which a sample passes through. Some flow chambers are blocks with channels through which samples can pass through. Some embodiments of the present invention may be called a parallel-plated flow chamber. However, other types of flow chambers are envisioned as embodiments of the present invention.

Figure 3:
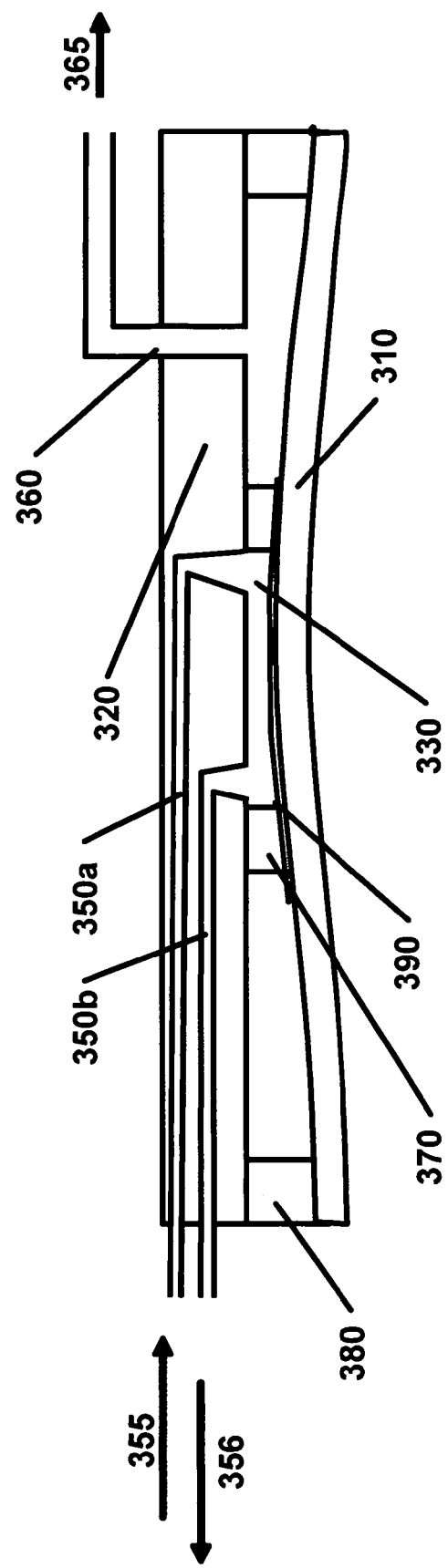
FIG. 3 is a schematic diagram of a third embodiment of the present invention.

FIG. 3 is a schematic diagram of a third embodiment of a flow chamber. The placement of two openings 350a and 350b may be modified as long as they communicate with the specimen chamber 330. At least a portion of the first member 310 should be flexible, which means the whole first member or only a section of the first member should be flexible. However, both members 310, 320 may be flexible. The inner spacer 370 is thinner than the outer spacer 380 in this embodiment. The thickness of inner spacer 370 contributes to the thickness of the specimen chamber 330. In this embodiment, a substrate base 390 is bigger in size than the inner spacer 370. The thickness of the inner spacer 370 may be adjusted to accommodate substrate bases of different size. The specimen chamber is defined by the substrate base 390, the inner spacer 370, the first member 310 and the second member 320. In certain cases, the fluid might not come in contact with the first member 310 because the substrate base 390 is made of impermeable substance. In such a case, the section of the substrate base 390 inside the inner spacer 370 may be considered to be a part of the specimen chamber 330, and the specimen chamber may still be defined by the first member 310, the inner spacer 370 and the second member 320. The substrate base 390 may be determined by scientists or other users for each type of assay they would like to conduct. Substrate bases of various sizes and shapes may be used with this embodiment.

Figure 4:
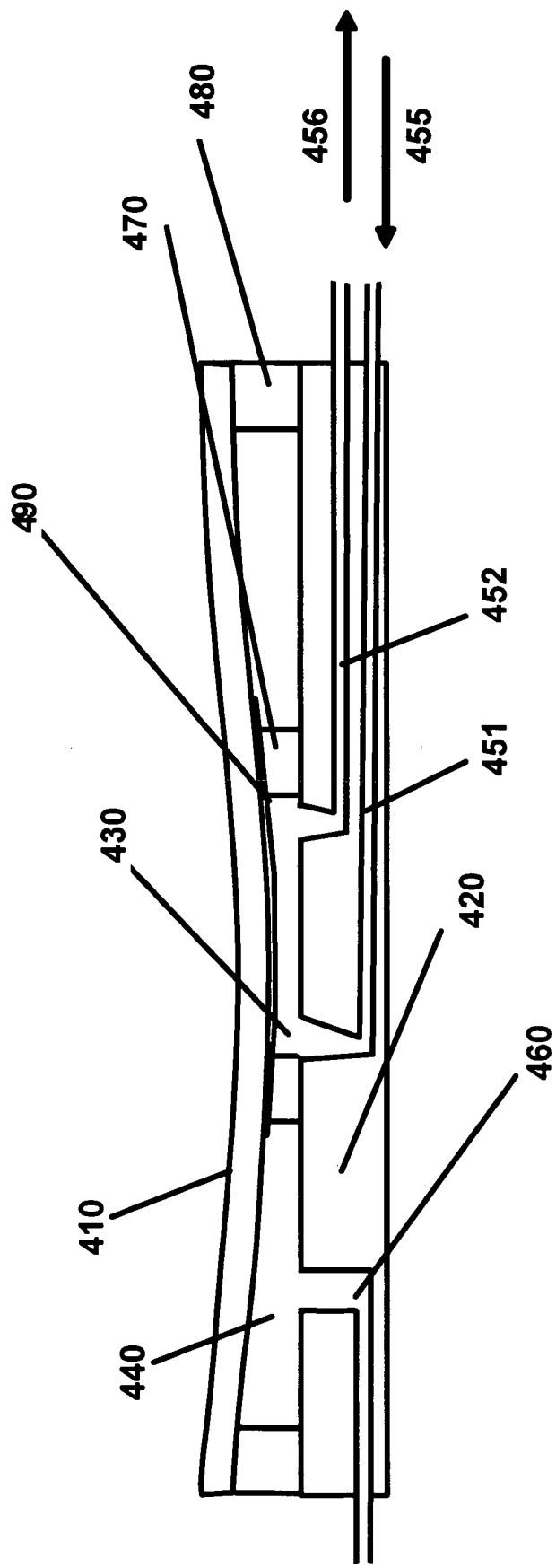
FIG. 4 is a schematic diagram of a fourth embodiment of the present invention.

FIG. 4 is a schematic diagram of a fourth embodiment of a flow chamber. The second member 420 has channels that serve as an inlet 451 and an outlet 452 of specimen chamber 430, and an opening 460 that communicates with the vacuum chamber 440. If a microarray is necessary for an assay, a microarray 390 may be inserted on the top of inner spacer 470. The first member 410 may have a very simple design. It may be a thin, flexible, transparent plate. The movements of fluid into and out of the specimen chamber 430 are shown with arrows 455 and 456.

Some embodiments of the present invention may be used with microfluidic chips. Microfluidic chips have a system of narrow channels or chambers built into a chip through which a sample or fluid flows. Arrangement of channels may vary to control the rate of flow or to mix certain amount of reagents. Some microfluidic chips may also have arrays of microelectrodes as an integral part. Microfluidic chips may alternatively be called microchips or microflow chips.

Figure 5:
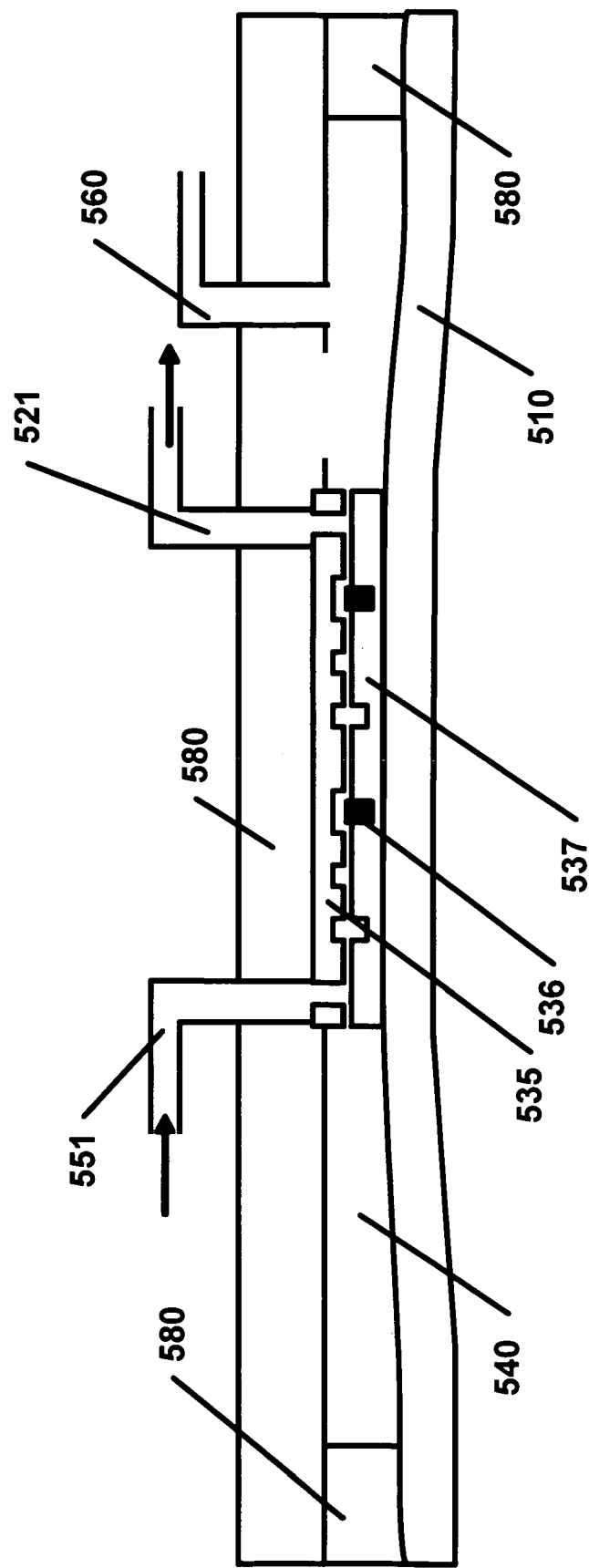
FIG. 5 is a schematic diagram of a fifth embodiment of the present invention.

FIG. 5 is a schematic diagram of a fifth embodiment of a flow chamber. In this embodiment, a microfluidic chip is positioned inside a flow chamber. The microfluidic chip is made of an upper-plate 535 and a lower-plate 537. Arrays of electrodes 536 are located on lower-plate 537. There may not be a need for an inner O-ring. The channels inside the microfluidic chip serves as the specimen chamber. A vacuum may be created by evacuating the contents of the vacuum chamber 540 through a third opening 560. The vacuum should hold upper plate 535 and lower plate 537 together. The sample fluid may flow in through the first opening 551, flow through the channels of the microfluidic chip between upper plate 535 and lower plate 537, and exit through the second opening 552. The design and components of a microfluidic chip may differ, depending on the experiment or use that is being performed. Also, additional openings may be made on the first member 510 or the second member 520 if the use of a particular microfluidic chip requires more openings.

Figure 6A:
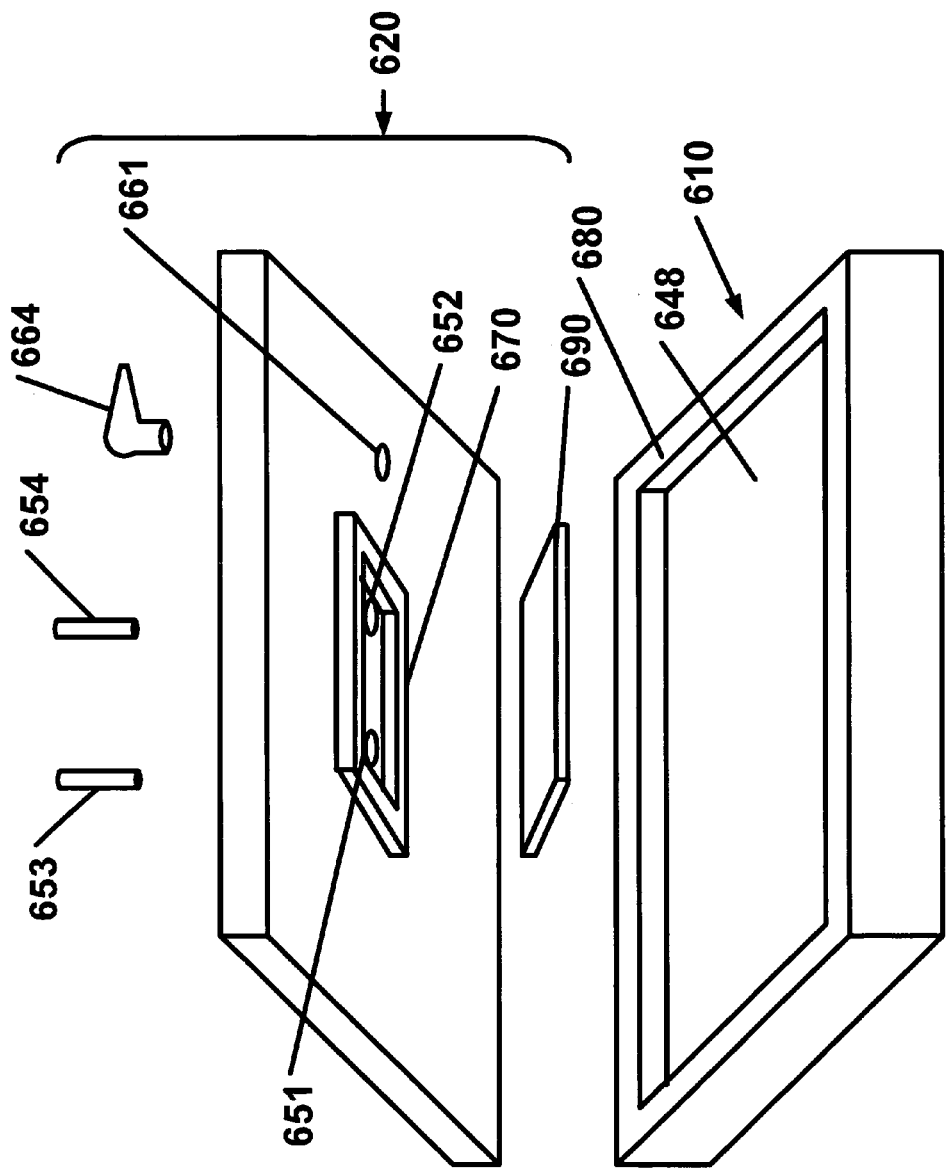
FIG. 6A is an exploded perspective view of a sixth embodiment of the present invention.

FIG. 6A is an exploded perspective view of a sixth embodiment. The first member 610 is a flexible plate with a shadow depression 648. A substrate base 690 may be placed on the middle of the depression 648. As shown, the second member 620 has three holes 651, 652, and 661. Holes 651 and 652 may serve as an inlet and an outlet for a specimen chamber. Hole 661 may serve as an opening for a vacuum chamber. The second member 620 has a spacing portion 670. Portion of hypodermic needles or tubes 653 and 654 may be glued to holes 651 and 652 to provide an easy way to add fluid to the flow chamber. Tubes 653 and 654 may be made of many materials such as steel, stainless steel or plastic. A nozzle 664 may be glued to hole 661. The microarray 690 covers a larger area than the spacing portion 670. When in operation, the spacing portion 670 on the bottom side of the second member 520 presses down on the substrate base 690 to keep the specimen chamber air-tight. Alternatively, a small substrate base may be glued to the first member 610, or a porous gel may be used to fill the specimen chamber.

Figure 6B:
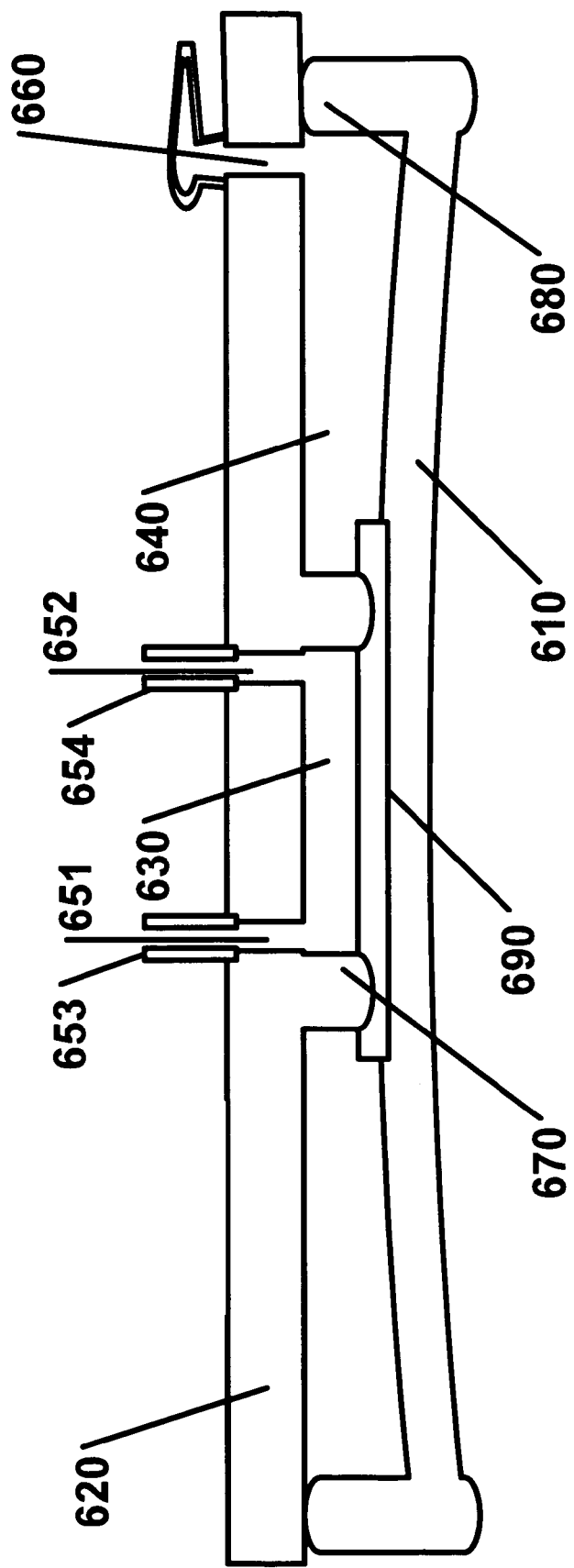
FIG. 6B is a sectional view of the sixth embodiment of the present invention.

FIG. 6B is a sectional view of the sixth embodiment of a flow chamber. In this embodiment, a first member 610 has spacing portions 680. A second member 620 has spacing portion 670. Separate O-rings may not be necessary. The first member 610 may be made of flexible and elastic material. A substrate base 690 may be placed on the first member 610, and the spacing portion 670 placed above a substrate base 690. The vacuum chamber 640 communicates with an opening 660 through which the content of the vacuum chamber 640 may be evacuated. When a vacuum is created, the spacing portion 670 may press down on the substrate base 690 and seal the vacuum chamber 640. Samples may be added through tfirst opening 651, flow through specimen chamber 530, and exit through second opening 652.

Figure 7A:
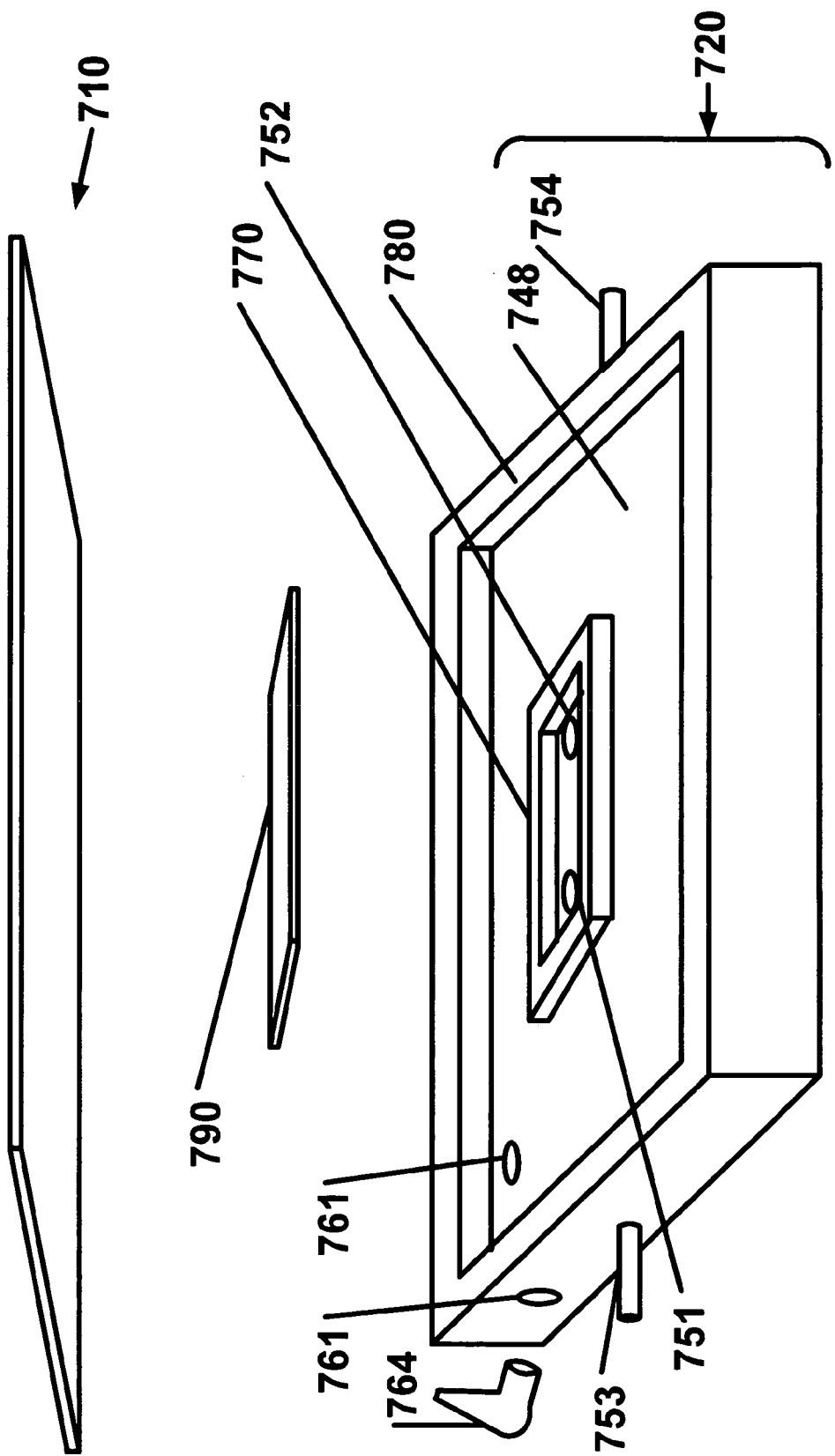
FIG. 7A is an exploded perspective view of a seventh embodiment of the present invention.

FIG. 7A is an exploded perspective view of a seventh embodiment. The first member 610 may be a thin, flexible plate. To use this embodiment as a specimen mount on a microscope, a plastic coverslip, a microscopic slide, or other thin and transparent material may be used. The seventh embodiment may also be made bigger, for example as a perfusion chamber. A substrate base 790 may be mounted on the top of an inner spacing portion 770 on a second member 720. As shown, the second member 720 has three holes 751, 752, and 761. Holes 751 and 752 may serve as an inlet and an outlet for a specimen chamber. Hole 761 may serve as an opening for a vacuum chamber. The second member 720 may have the inner spacing portion 770 inside a shadow depression 748 defined by an outer spacing portion 780. Tubes 753 and 754 can be glued to the outside of channels that extend from holes 751 and 752 to provide an easy way to add fluid to the flow chamber. Tubes 753 and 754 may be made of many materials including steel, stainless steel and plastic. Nozzle 764 may be glued to the outside of the channel that extends from hole 761. Although a nozzle 764 was used as an example, other ways may be used to couple the vacuum chamber to a vacuum source.

Figure 7B:
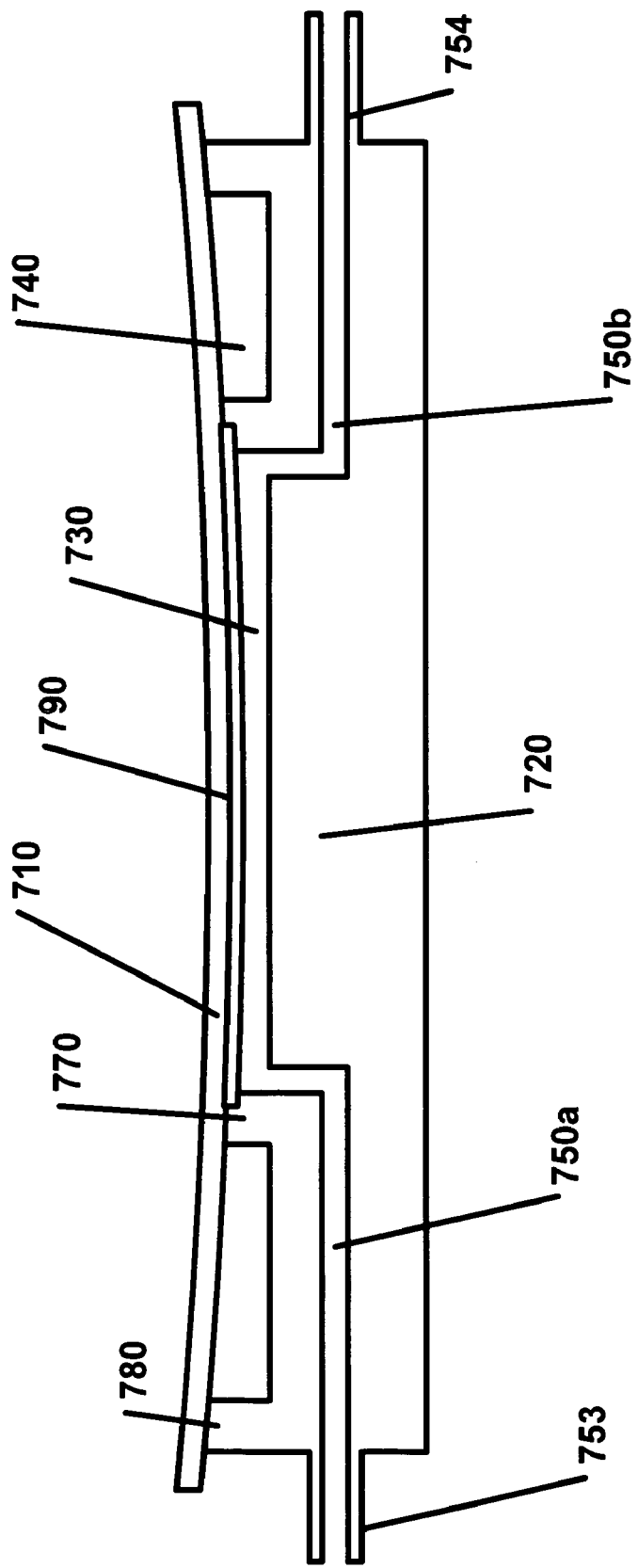
FIG. 7B is a sectional view of the seventh embodiment of the present invention.

FIG. 7B is a sectional view of the seventh embodiment of a flow chamber. The second member 720 may have channels that serve as an inlet 750*a* and an outlet 750*b* to specimen chamber 730. A second member 720 may have spacing portions 770 and 780.

The seventh embodiment may be made with three coverslips and a microscopic slide. For example, the first member 710 may be made from coverslips that are approximately 0.13 mm-0.5 mm in thickness, 25 mm in width, and 30 mm in length. The second member 720 may be made from two coverslips and a microscopic slide. Holes may be made on the slide and one or both of coverslips and glued together. Elastic materials may be attached to serve as spacing portions. The second member 720 may also be made by casting a synthetic material into a mold or by milling a plastic block and attaching elastic materials to serve as spacing portions. As demonstrated above, there are numerous ways to make this embodiment. Additionally, it is envisioned that the dimension may be varied to fit specific uses.

Figure 8A:
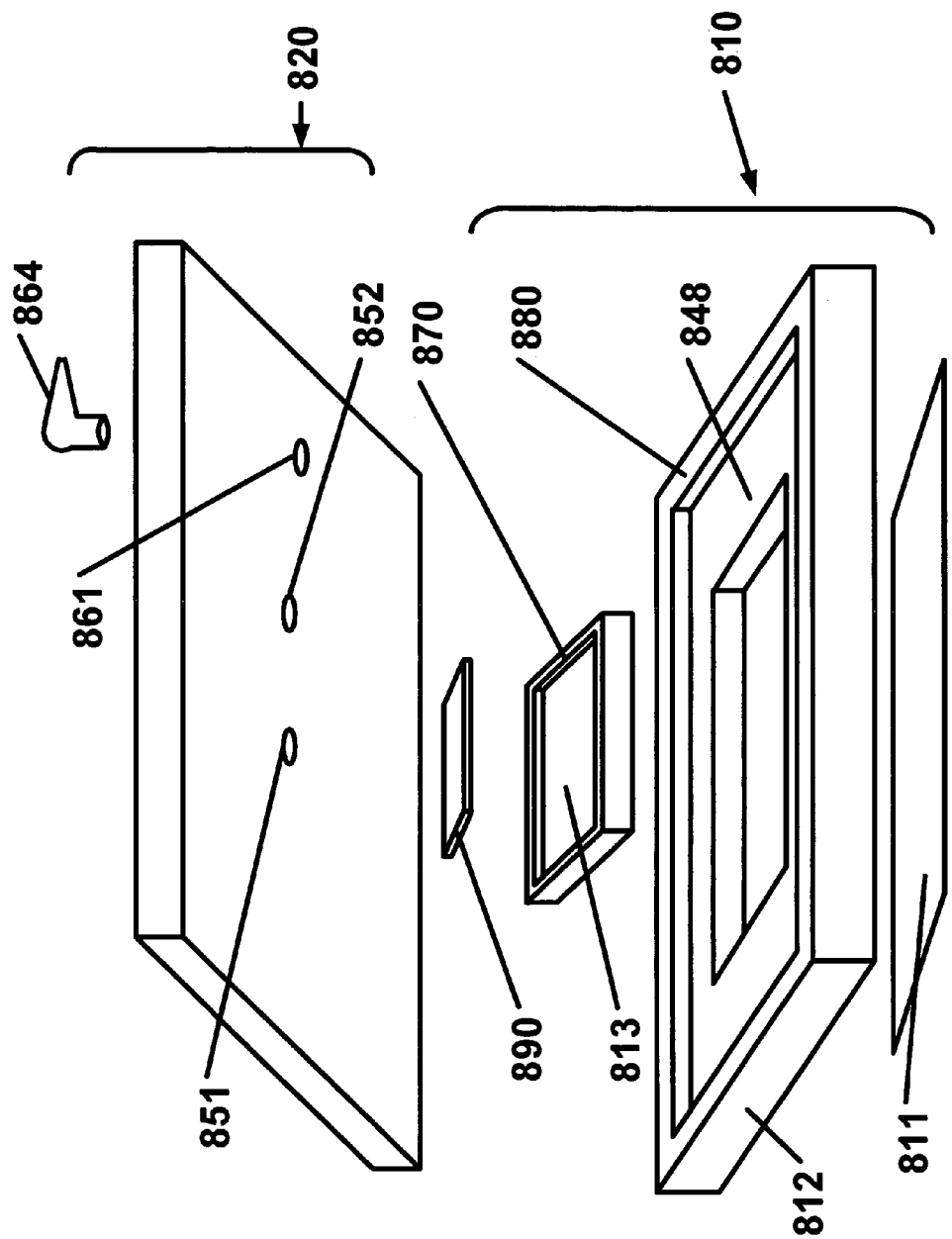
FIG. 8A is an exploded perspective view of an eighth embodiment of the present invention.

FIG. 8A is an exploded perspective view of an eighth embodiment. As shown, the second member 820 has three holes 851, 852 and 861. Holes 851 and 852 may serve as an inlet and an outlet for a specimen chamber. Hole 861 may serve as an opening for a vacuum chamber. Nozzle 864 may be attached to hole 861 to control the flow of air out of the vacuum chamber. First member 810 may be made from a flexible sheet 811, a small inner plate 813, and an outer plate 812. The inner plate 813 and the outer plate 812 may be glued to the flexible sheet 811. Because inner plate 813 is smaller than the hole inside the outer plate 812, a portion of the flexible sheet 811 is exposed to the vacuum chamber. If a microarray is necessary for an assay, a microarray 890 may be glued or fix in other ways inside the inner plate 813.

Figure 8B:
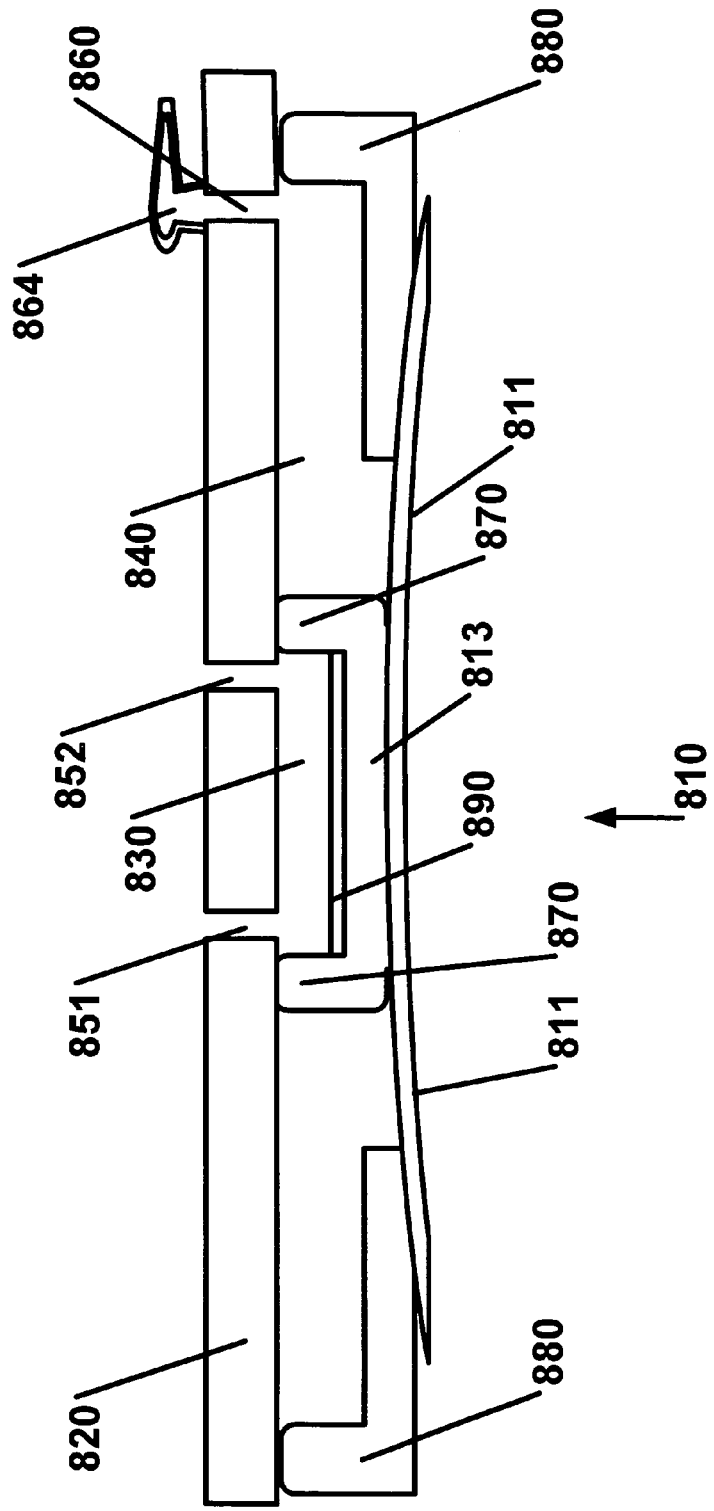
FIG. 8B is a sectional view of the eighth embodiment of the present invention.

FIG. 8B is a sectional view of the eighth embodiment of a flow chamber. The flexible sheet 811 may be deformed when the content of the vacuum chamber 840 is evacuated through nozzle 864. The height of the spacing portion 870 may control the height of the specimen chamber 830.

As an example, first member 810 may be made using a microscopic slide or other transparent plate such as a plastic, glass, or polymer plate. A donut shaped frame may be cut out of a transparent plate to make the outer plate 812. A smaller section may be cut out of a transparent plate to make inner plate 813. These two pieces may be placed on a polymer tape, or glued on other transparent and flexible sheet 811. An elastic material may be attached to the inner plate 813 to serve as an inner spacing portion 870. An elastic material may be attached to the outer plate 812 to serve as an outer spacing portion 880.

Figure 9A:
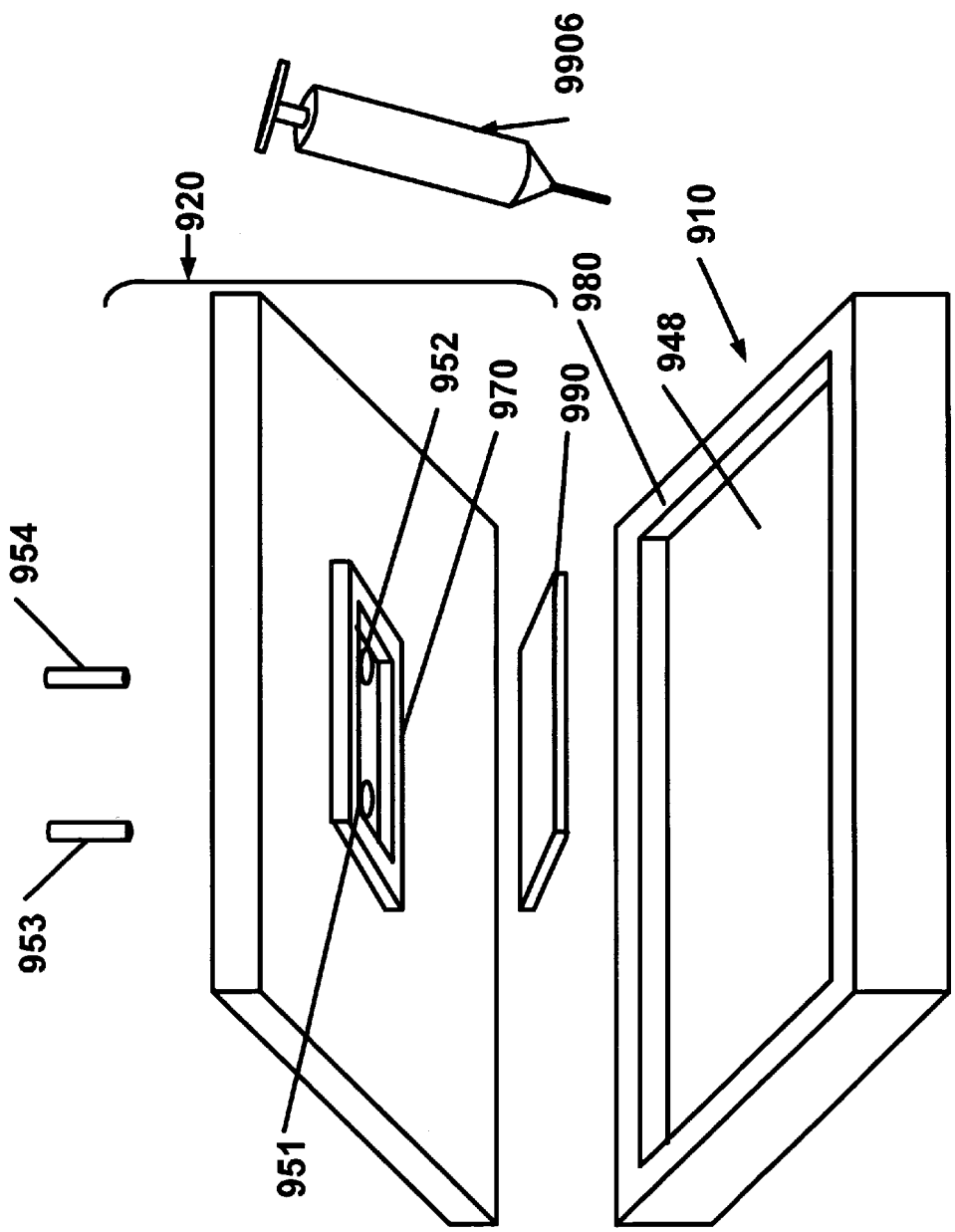
FIG. 9A is an exploded perspective view of a ninth embodiment of the present invention.

FIG. 9A is an exploded perspective view of a ninth embodiment. As shown, the second member 920 has two holes 951 and 952 which may serve as an inlet and an outlet for a specimen chamber. There may not be a permanent opening that communicates with a vacuum chamber. Instead a syringe 9906 may be used to make an opening when the contents of the vacuum chamber should be evacuated. The second member 920 may have an inner spacing portion 970 which defines the specimen chamber. The first member 910 may have a spacing portion 980 and a shallow depression 948. A substrate base 990 may be placed on the shallow depression as necessary. A portion of the first member 910 may be made of a substance that allows the needle of the syringe 9906 to penetrate.

Figure 9B:
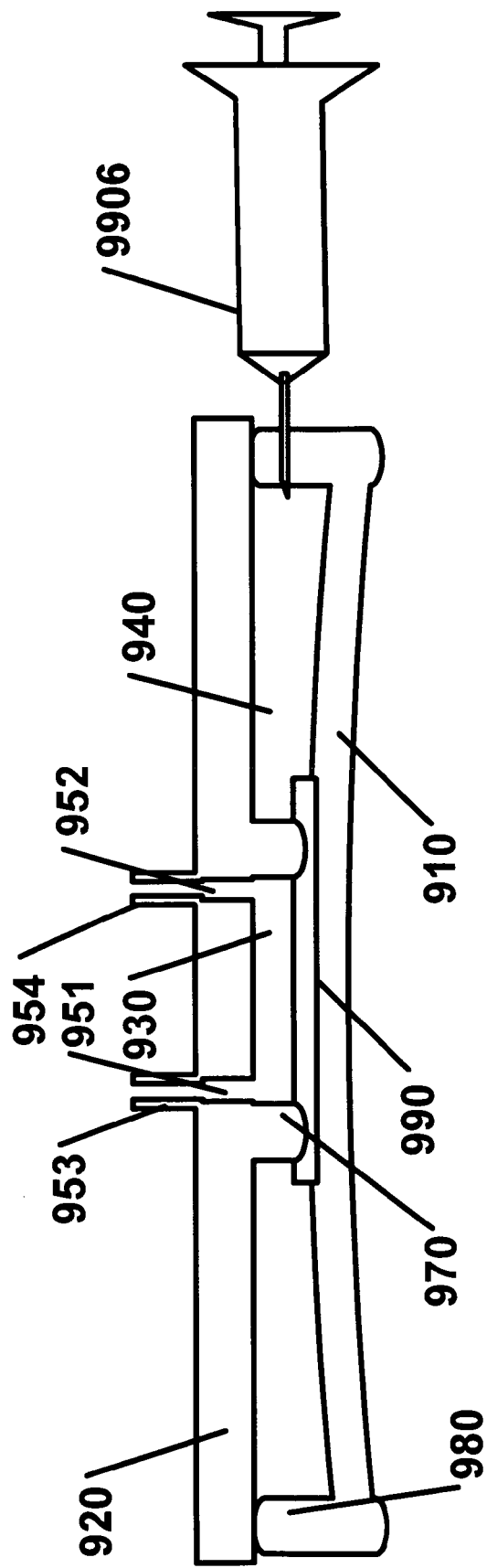
FIG. 9B is a sectional view of the ninth embodiment of the present invention.

FIG. 9B is a sectional view of the ninth embodiment. The needle of syringe 9906 may bes inserted into the first member 910 to evacuate the contents of the vacuum chamber 940. The first member 910 should then deform by the atmospheric pressure imposed on the flow chamber.

Figure 10A:
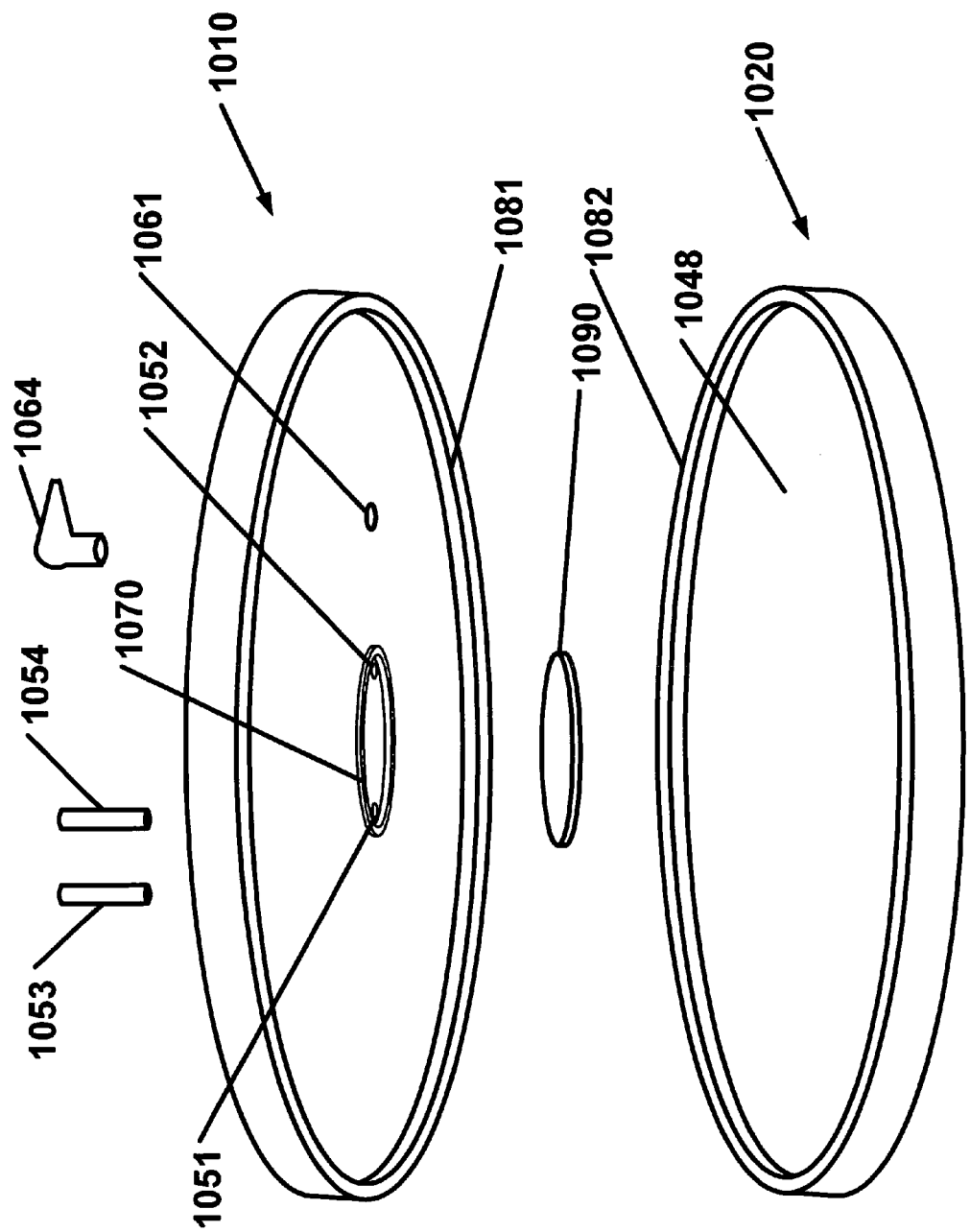
FIG. 10A is an exploded perspective view of a tenth embodiment of the present invention.

FIG. 10A is an exploded perspective view of a tenth embodiment. The first member 1010 and the second member 1020 may be oval in shape. The first member 1010 may have spacing portions 1070 and 1081. The second member 1020 may have spacing portion 1082 which comes in contact with the spacing portion 1081 when the embodiment is assembled. As shown, the first member 1010 has three holes 1051, 1052 and 1061 which may serve as an inlet and an outlet for a specimen chamber and an opening for a vacuum chamber. Tubes 1053 and 1054 may be attached to the outside of the channel that extends to holes 1051 and 1052. A nozzle 1064 may be attached to the channel that extends to the hole 1061. A substrate base 1090 may be used with the flow chamber. Both the first member 1010 and the second member 1020 may be made of flexible material.

Figure 10B:
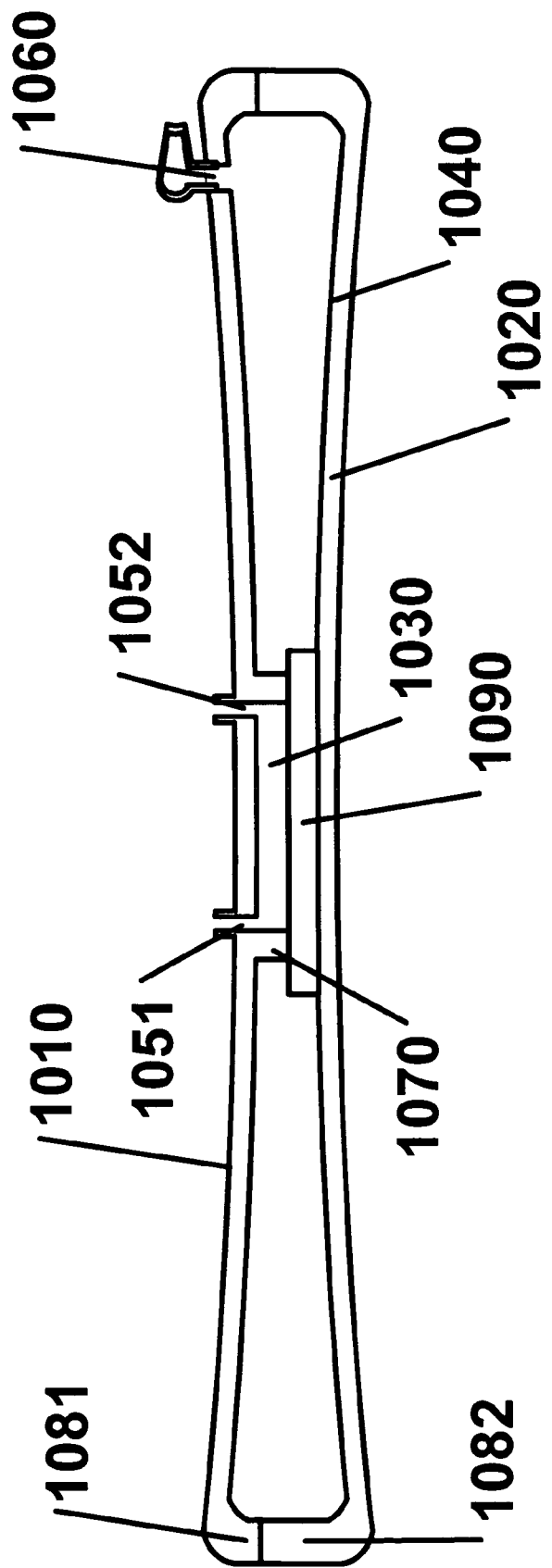
FIG. 10B is a sectional view of the tenth embodiment of the present invention.

FIG. 10B is a sectional view of the tenth embodiment. When the content of the vacuum chamber 1040 is evacuated, both the first member 1010 and the second member 1020 may deform to create a specimen chamber 1030. One way to make this embodiment is to cast a polymer into a mold. It will be apparent to a person skilled in the art that there are other ways to make this embodiment.

Figure 11A:
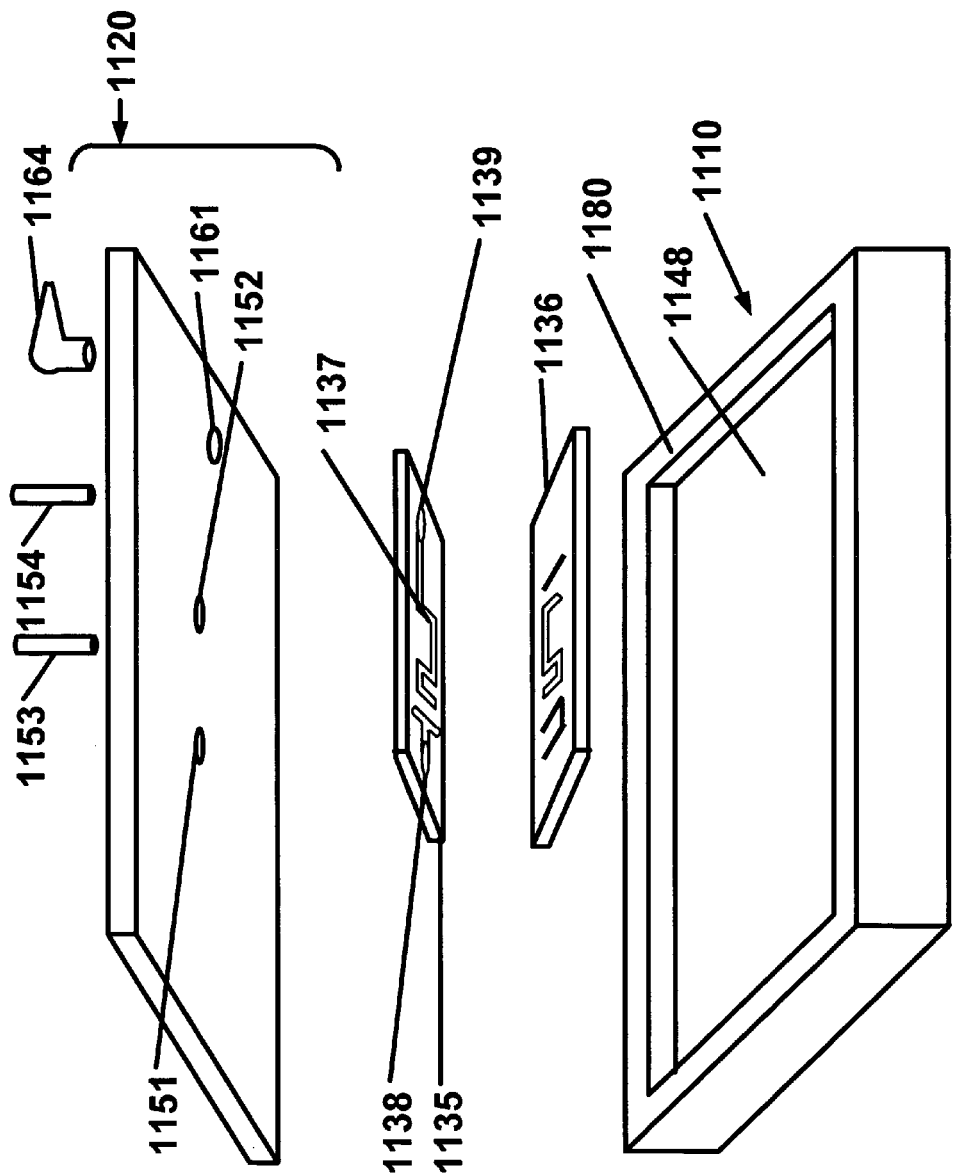
FIG. 11A is an exploded perspective view of an eleventh embodiment of the present invention.

FIG. 11*a* is an exploded perspective view of an eleventh embodiment. First member 1110 may have a spacing portion 1180 which forms a shallow depression 1148. A microfluidic chip may be placed inside the depression 1148. The microfluidic chip shown has an upper plate 1135 and a lower plate 1136. The upper plate 1135 may have grooves 1137 and holes 1138 and 1139 through which a fluid sample may flow in and out. The lower plate 1136 may also have a combination of grooves and patterns of substances embedded into a microfluidic chip. This microfluidic chip is shown as an example only. Microfluidic chips are commercially available in a variety of shapes and sizes from companies such as NSG Precision Cells, Inc. of Farmingdale, N.Y., and Micralyne Inc. of Edmonton, Alberta in Canada. Variations may be made to the first member 1110 or the second member 1120 to accommodate microfluidic chips of different size, shape, and use. The second member may have two or more openings 1151 and 1152 which communicates with the holes 1138 and 1139 on the microfluidic chip. Samples may be added through the tube 1153, into the hole 1138 on the microfluidic chip, flow through the grooves 1137, and exit through the hole 1139 and the tube 1154. In this embodiment, a portion of the first member 1110 may be flexible. However, it is possible to make other embodiments of the present invention by making a portion of the second member also flexible. The second member 1120 may have a hole 1161 through which the vacuum chamber can be evacuated.

Figure 11B:
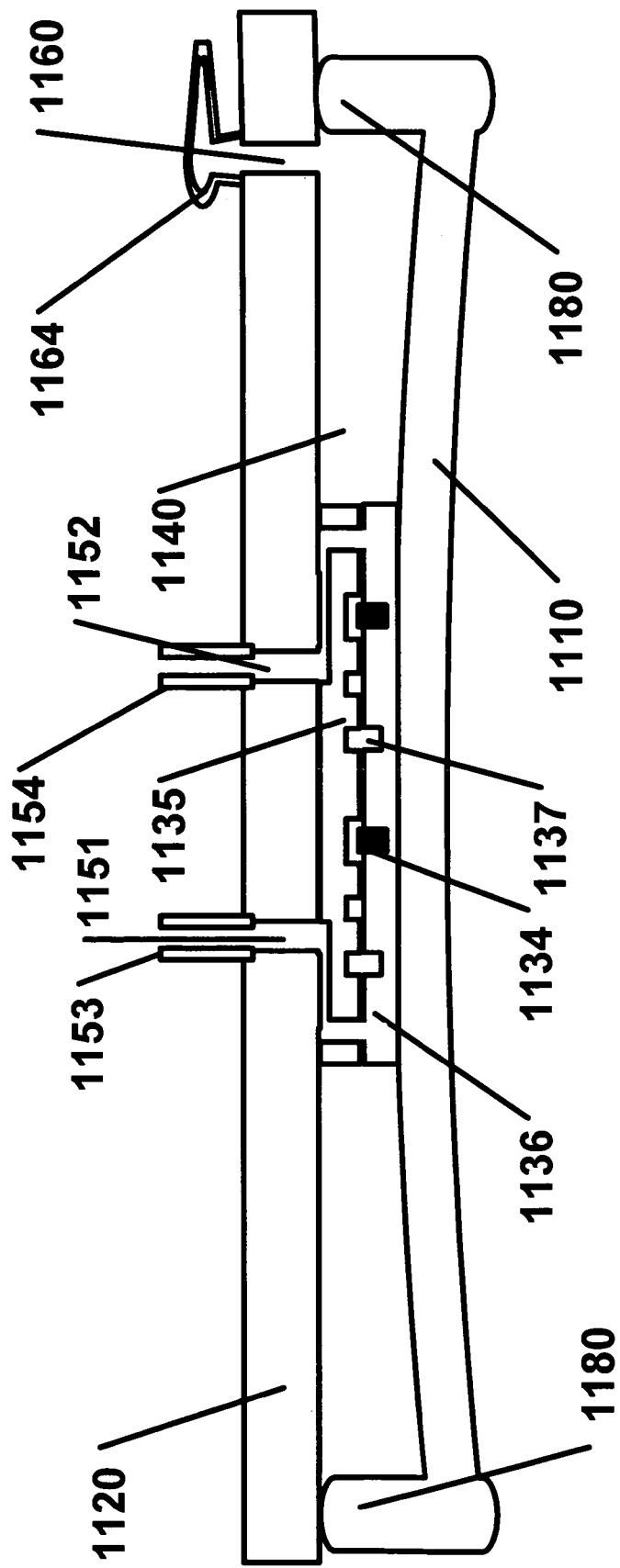
FIG. 11B is a sectional view of the eleventh embodiment of the present invention.

FIG. 11B is a sectional view of the eleventh embodiment. As shown, the contents of the vacuum chamber 1140 are already withdrawn through an opening 1160 on the second member 1120. The upper plate 1135 and the lower plate 1136 of the microfluidic chip are in contact, forming channels 1137 through which a fluid sample may pass. The microfluidic chip may also have other material embedded. An array of electrode 1134 is shown in FIG. 11B.

Figure 12:
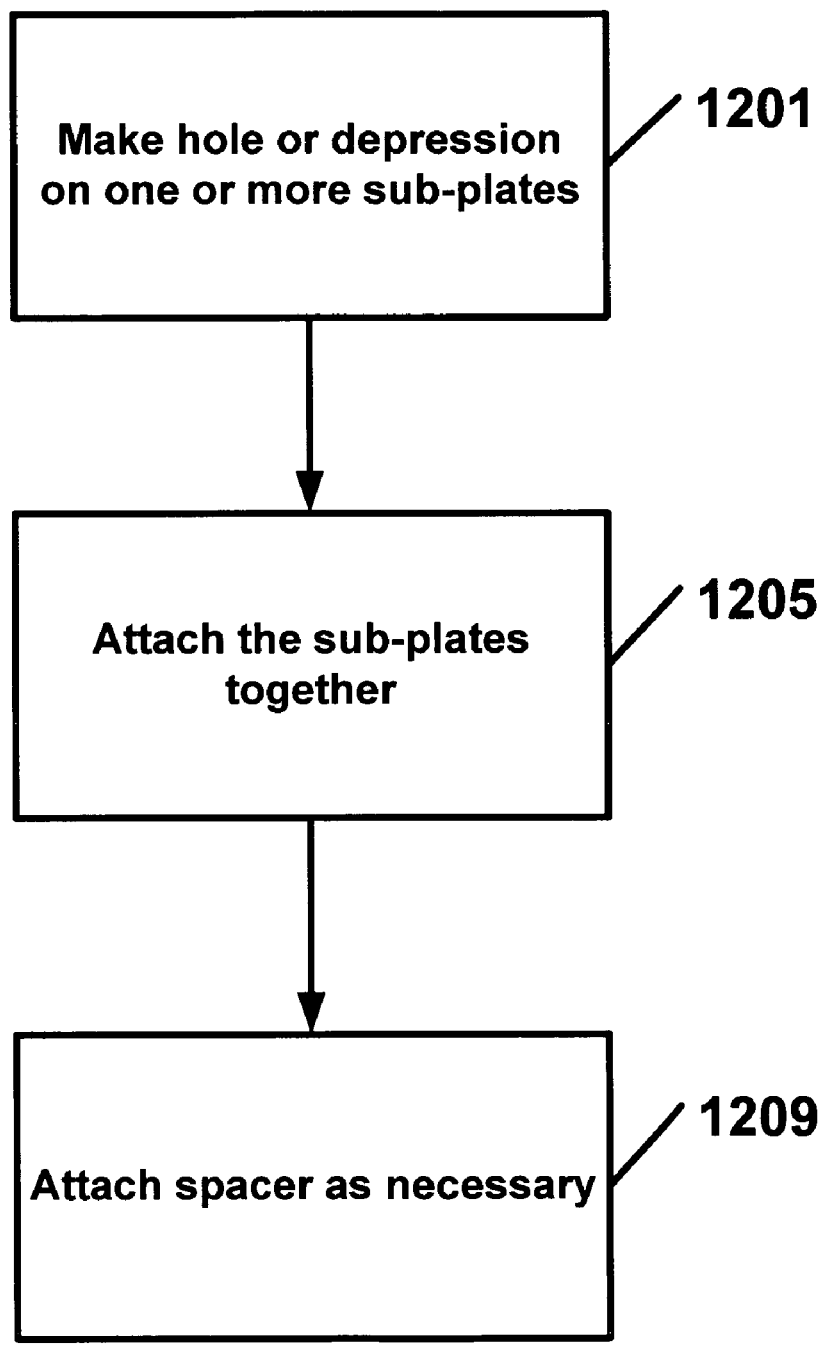
FIG. 12 is a system diagram of a way of making either a first member or a second member of a twelfth embodiment of the present invention.

FIG. 12 is a flow diagram showing a way of making either a first member or a second member of a twelfth embodiment of the present invention. Two or more sub-plates are necessary to make the member, although not all of the sub-plates have to have hole or depression. At 1201, one or more hole(s) or depression(s) may be made on one or more sub-plate. The hole may be made in a variety of ways. If the sub-plate is glass or plastic, the sub-plate may be covered with wax, a line or a point may be scratched on the wax coating, and the waxed sub-plate may be exposed to concentrated hydrofluoric acid. A plastic material may also be milled to make a groove, hole, or depression.

At 1205, the sub-plates may be attached together. Some sub-plates may be sticky on one side, and putting the plates together will joint them together. Transparent glue may be used. In some cases, the sub-plates may be put together by heating them together. Other ways of putting the sub-plates together may be used.

After the sub-plates are attached together, if a necessary spacing portion is not already present, one or more spacers may be attached to the sub-plates at 1209. Many elastic and non-elastic materials may serve as a spacer. A polymer tape may be attached without using glue.

Figure 13:
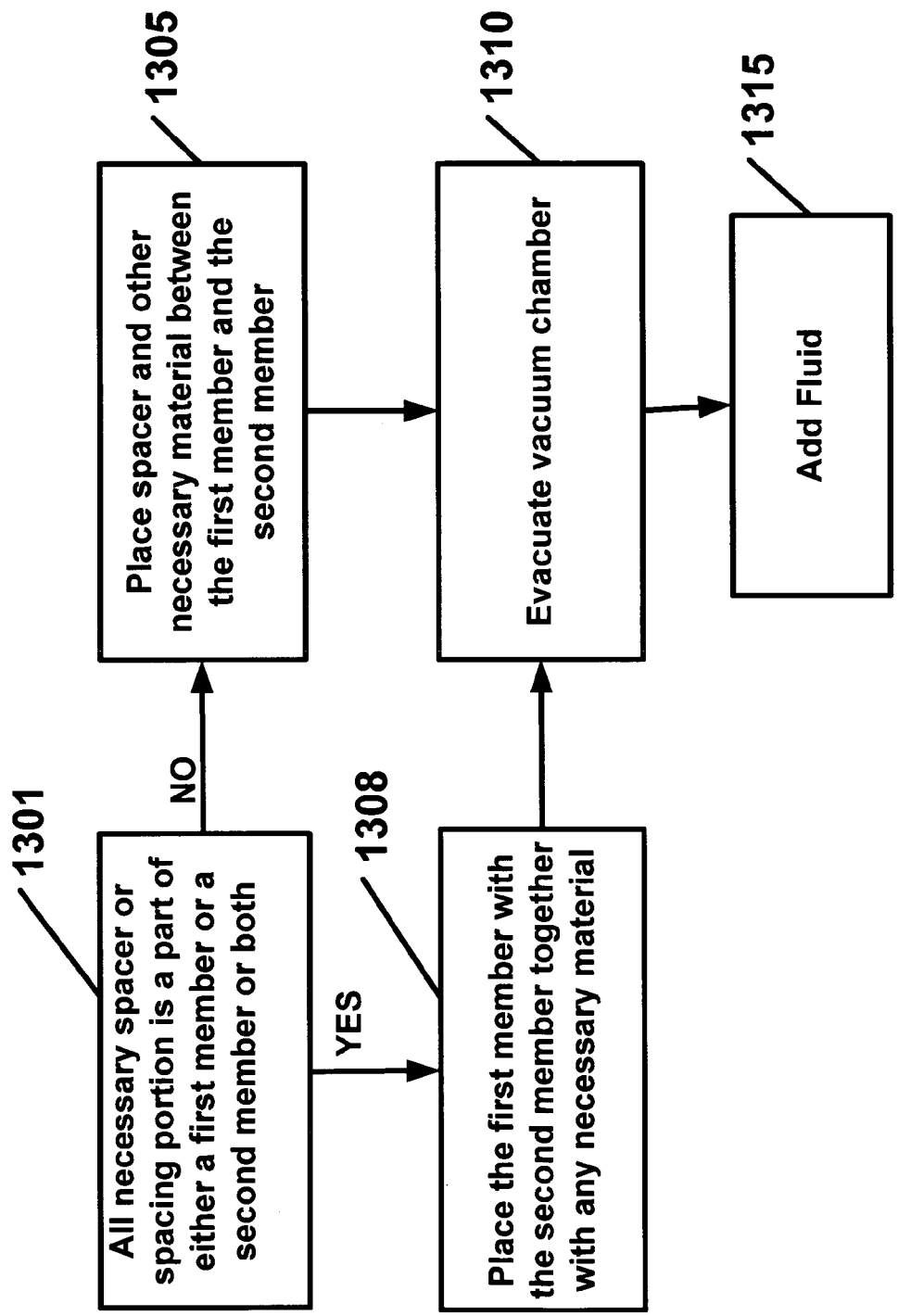
FIG. 13 is a system diagram of a way of preparing a thirteenth embodiment of the present invention for an assay.

FIG. 13 is a flow diagram showing a way of preparing a thirteenth embodiment for an assay. A first member or a second member or both may already have all necessary spacer or spacing portion attached to it. If the spacer or spacing portions are already present and if other material is necessary for an assay, place a substrate base or other necessary material in between the first member and the second member at 1308. Materials that might be added include a substrate base, cell cultures for a perfusion chamber, microfluidic chip for certain experiments, regents, or other appropriate material for the particular assay. If no other materials are necessary, the first member may be joined with the second member.

If a necessary spacing portion or spacer is not already present on either the first member or the second member, the spacer should be placed with other necessary material in between the first member and the second member according at 1305.

After putting the first member and the second member together at either 1305 or 1308, the vacuum chamber may be evacuated at 1310. There are a numerous ways to create a vacuum. There are commercial vacuum pumps. A syringe can be used if the first member or the second member is made of a substance that can be penetrated by a syringe needle. Many chemical labs are equipped with vacuum filtration system. After the vacuum chamber is evacuated, fluid can be added to the specimen chamber.

While various embodiments of the present invention have been described above, it should be understood that they have been presented by way of example, and not limitation. It will be apparent to persons skilled in the relevant art that various changes in form and detail can be made therein without departing from the spirit and scope of the present invention. In fact, after reading the above description, it will be apparent to one skilled in the relevant art how to implement the invention in alternative embodiments. Thus, the present invention should not be limited by any of the above described exemplary embodiments. In particular, it should be noted that, for example purposes, the above explanation has focused on the examples of 13 specific embodiments. However, those experienced in the art will realize that multiple other embodiments, including, but not limited to ones disclosed, can be used.

In addition, it should be understood that any figures, schematic diagrams, system diagrams, or examples which highlight the functionality and advantages of the present invention, are presented for example purposes only. The architecture of the present invention is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope of the present invention in any way.

Furthermore, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

The present invention can be made from a variety of materials, in a variety of shape and size, for a variety of purpose. The scope of the present invention is limited only by the claims as follows.

What is claimed is:

1. A flow chamber, comprising:
    a first member having a flexible portion; and
    a second member, wherein either the first member or the second member or both has a spacing portion, the spacing portion comprising a first part separating the members a first distance and a second part separating the members a second distance different than the first distance, wherein the first member and the second member define a first chamber having a first opening and a second opening and a second chamber having a third opening, wherein evacuation of the second chamber deforms the flexible portion, seals the first chamber and causes at least the first member and the second member to be held together.

2. A flow chamber according to claim 1, wherein the spacing portion comprises an inner O-ring and an outer O-rings displaced in a concentric arrangement, wherein the inner O-ring comprises the first part and the outer O-ring comprises the second part.

3. A flow chamber according to claim 1, further including a substrate base disposed inside the first chamber.

4. A flow chamber according to claim 1, further including a microarray disposed between the first member and the second member.

5. A flow chamber according to claim 1, wherein at least one of:
    the first part comprises a smaller cross-sectional area than the second part, wherein the first distance is smaller than the second distance; and the first part on a different plane than the second part between the members, wherein the first distance is smaller than the second distance.

6. A flow chamber, comprising:
a first member having a flexible portion;
a second member disposed near the first member; and
a spacer comprising a first part separating the members a first distance and a second part separating the members a second distance different than the first distance, wherein the spacer, the first member, and the second member define two chambers, wherein the first chamber communicates with a first opening and a second opening, and the second chamber communicates with a third opening, wherein the first chamber is sealed through deformation of the flexible portion and at least the first member and the second member are held together by pressure.

7. A flow chamber according to claim 6, wherein the spacer comprises two O-rings.

8. A flow chamber according to claim 6, wherein the spacer comprises an O-ring, and wherein a microfluidic chip sits on either the first member or the second member.

9. A flow chamber according to claim 6, wherein:
the first chamber and the second chamber are disposed in a concentric arrangement; and
the first chamber is substantially surrounded by the second chamber.

10. A flow chamber according to claim 6, further including a substrate base which is detachably disposed within the first chamber.

11. A flow chamber according to claim 6, wherein the third opening is coupled to a vacuum source.

12. A flow chamber according to claim 6, wherein the first opening is coupled to a sample source and the second opening is coupled to a sample waste.

13. A flow chamber according to claim 6, further including a magnetic device disposed near the first chamber to create a magnetic field.

14. A flow chamber according to claim 6, wherein a portion of at least one of the first member and the second member is transparent.

15. A flow chamber according to claim 6, wherein the flow chamber is adapted to be mounted on an optical microscope.

16. A flow chamber according to claim 15, wherein the second member comprises two or more transparent sub-plates glued together, wherein one or more of the sub-plates has a hole or depression which serves as at least one of the openings.

17. A flow chamber according to claim 15, wherein the microscope objective approaches the first chamber by 0.13 mm or less while providing a free lateral space of at least 20 mm in diameter.

18. A flow chamber according to claim 15, wherein the microscope illuminator approaches the first chamber by 0.5 mm or less while providing a free lateral space of at least 20 mm in diameter.

19. A method for preparing a flow chamber for an assay, comprising:
placing a first member and a second member together including a spacer therebetween, the spacer comprising a first part separating the members a first distance and a second part separating the members a second distance different than the first distance; forming a first chamber having a first opening and a second opening, and a second chamber having a third opening; and evacuating the second chamber to cause at least the first member and the second member to be held together.

20. A method for preparing a flow chamber according to claim 19, wherein the placing step involves placing a spacer between the first member and a second member.

* * * * *